(12) United States Patent
Kopelman

(10) Patent No.: US 11,395,593 B2
(45) Date of Patent: Jul. 26, 2022

(54) DEVICE, SYSTEM AND METHOD FOR DETECTING IRREGULARITIES IN SOFT TISSUE

(71) Applicant: Mor Research Applications Ltd., Tel-Aviv (IL)

(72) Inventor: Doron Kopelman, Caesarea (IL)

(73) Assignee: Mor Research Applications Ltd., Ramat Gan (IL)

( * ) Notice: Subject to any disclaimer, the term of this patent is extended or adjusted under 35 U.S.C. 154(b) by 695 days.

(21) Appl. No.: 16/332,794

(22) PCT Filed: Sep. 9, 2017

(86) PCT No.: PCT/IB2017/055448
§ 371 (c)(1),
(2) Date: Mar. 13, 2019

(87) PCT Pub. No.: WO2018/051220
PCT Pub. Date: Mar. 22, 2018

(65) Prior Publication Data
US 2019/0357774 A1   Nov. 28, 2019

Related U.S. Application Data

(60) Provisional application No. 62/394,327, filed on Sep. 14, 2016.

(51) Int. Cl.
*A61B 5/00* (2006.01)
*A61B 5/145* (2006.01)
*A61B 5/1477* (2006.01)

(52) U.S. Cl.
CPC .......... *A61B 5/0091* (2013.01); *A61B 5/0053* (2013.01); *A61B 5/0057* (2013.01);
(Continued)

(58) Field of Classification Search
CPC ... A61B 5/0091; A61B 5/0053; A61B 5/0057; A61B 5/0077; A61B 5/14507;
(Continued)

(56) References Cited

U.S. PATENT DOCUMENTS 4,190,058 A * 2/1980 Sagi ....................... A61B 5/015
600/549
4,250,894 A   2/1981 Frei et al.
(Continued)

FOREIGN PATENT DOCUMENTS

WO   WO 2018/051220   3/2018

OTHER PUBLICATIONS

International Search Report and the Written Opinion dated Dec. 17, 2017 From the International Searching Authority Re. Application No. PCT/IB2017/055448. (9 Pages).

*Primary Examiner* — May A Abouelela

(57) ABSTRACT

According to some embodiments there is provided a wearable device for breast screening, comprising: at least one breast-contacting member shaped to contact a surface of a breast, the member comprising an array of force applying units and an array of sensors configured for sensing at least one parameter in response to force applied by the force applying units; the force applying units and the sensors disposed on or within the breast-contacting member and positioned to contact a surface of the breast; a memory storing one or more patterns suitable to detect a lump underlying the surface; wherein the pattern comprises a sequence of forces that vary spatially and/or vary in time; a controller configured for: reading data from the memory to control application of force; communicating with the sensors to receive signals associated with the at least one parameter sensed in response to the application of force; and to process the received signals to detect a lump.

20 Claims, 14 Drawing Sheets

(52) U.S. Cl.
CPC .......... *A61B 5/0077* (2013.01); *A61B 5/1477* (2013.01); *A61B 5/14507* (2013.01); *A61B 5/4887* (2013.01); *A61B 5/6804* (2013.01); *A61B 2562/0247* (2013.01)

(58) Field of Classification Search
CPC ... A61B 5/1477; A61B 5/4887; A61B 5/6804; A61B 2562/0247; A61B 5/4312
USPC .................................................. 600/587, 595
See application file for complete search history.

(56) References Cited

U.S. PATENT DOCUMENTS

| | | | |
|---|---|---|---|
| RE32,000 E | 10/1985 | Sagi | |
| 4,651,749 A * | 3/1987 | Sagi | A61B 5/015 600/549 |
| 5,301,681 A * | 4/1994 | DeBan | A61B 5/015 128/925 |
| 5,678,565 A * | 10/1997 | Sarvazyan | G01S 7/52042 600/587 |
| 5,785,663 A | 7/1998 | Sarvazyan | |
| 5,830,159 A * | 11/1998 | Netta | A61B 5/015 600/587 |
| 5,833,633 A | 11/1998 | Sarvazyan | |
| 5,833,634 A * | 11/1998 | Laird | A61B 5/0053 600/587 |
| 6,029,077 A * | 2/2000 | Wake | A61B 5/0091 33/512 |
| 6,077,228 A * | 6/2000 | Schonberger | A61B 5/015 374/100 |
| 6,086,247 A | 7/2000 | Von Hollen | |
| 6,419,636 B1 * | 7/2002 | Young | A61B 5/015 600/372 |
| 6,478,739 B1 | 11/2002 | Hong | |
| 6,595,933 B2 | 7/2003 | Sarvazyan et al. | |
| 6,620,115 B2 | 9/2003 | Sarvazyan et al. | |
| 8,597,234 B2 * | 12/2013 | Larsson | A61B 5/053 604/74 |
| 8,992,445 B2 * | 3/2015 | Blondheim | A61B 5/4878 600/587 |
| 10,398,816 B2 * | 9/2019 | Chang | A61M 1/74 |
| 2001/0031934 A1 * | 10/2001 | Sarvazyan | A61B 5/4312 600/587 |
| 2002/0076681 A1 | 6/2002 | Leight et al. | |
| 2002/0143275 A1 | 10/2002 | Sarvazyan et al. | |
| 2003/0073951 A1 * | 4/2003 | Morton | A61B 10/0041 604/73 |
| 2004/0157188 A1 | 8/2004 | Luth et al. | |
| 2004/0253652 A1 * | 12/2004 | Davies | A61B 5/4839 435/7.23 |
| 2004/0267165 A1 * | 12/2004 | Sarvazyan | A61B 5/0002 600/587 |
| 2005/0020921 A1 * | 1/2005 | Glassell | A61B 8/4483 600/463 |
| 2005/0059928 A1 * | 3/2005 | Larsson | A61B 5/053 604/74 |
| 2005/0197583 A1 * | 9/2005 | Chance | A61B 5/0091 600/476 |
| 2006/0167530 A1 | 7/2006 | Flaherty et al. | |
| 2006/0264745 A1 | 11/2006 | Da Silva | |
| 2007/0038152 A1 | 2/2007 | Sarvazyan et al. | |
| 2008/0289079 A1 | 11/2008 | Lewis | |
| 2009/0278798 A1 | 11/2009 | Kim et al. | |
| 2010/0080347 A1 * | 4/2010 | Kalender | A61B 6/035 378/37 |
| 2010/0198025 A1 | 8/2010 | Lindahl et al. | |
| 2010/0207490 A1 | 8/2010 | Chuang | |
| 2010/0263182 A1 | 10/2010 | Chuang | |
| 2010/0298895 A1 | 11/2010 | Ghaffari et al. | |
| 2011/0266923 A1 | 11/2011 | Chuang et al. | |
| 2012/0271141 A1 * | 10/2012 | Davies | A61B 5/4312 600/382 |
| 2012/0277636 A1 * | 11/2012 | Blondheim | A61B 5/742 600/595 |
| 2013/0070074 A1 | 3/2013 | Won | |
| 2013/0218045 A1 * | 8/2013 | Ironstone | A61B 5/4312 600/547 |
| 2015/0055746 A1 | 2/2015 | Lee et al. | |
| 2015/0073254 A1 * | 3/2015 | Talant | A41C 3/0064 600/407 |
| 2015/0320385 A1 | 11/2015 | Wright | |
| 2016/0206211 A1 * | 7/2016 | Naimi | G06T 7/0012 |
| 2016/0228008 A1 | 8/2016 | Lee | |
| 2016/0296135 A1 * | 10/2016 | Yoo | A61B 5/7225 |
| 2016/0310075 A1 * | 10/2016 | Ross | A61B 5/6898 |
| 2016/0349337 A1 * | 12/2016 | Park | A61B 5/6823 |
| 2017/0172502 A1 * | 6/2017 | Rote | G01L 1/2256 |
| 2017/0224223 A1 * | 8/2017 | Nishihara | A61B 5/0095 |
| 2017/0303793 A1 * | 10/2017 | Fukutani | A61B 5/708 |

* cited by examiner

DEVICE, SYSTEM AND METHOD FOR DETECTING IRREGULARITIES IN SOFT TISSUE

RELATED APPLICATIONS

This application is a National Phase of PCT Patent Application No. PCT/IB2017/055448 having International filing date of Sep. 9, 2017, which claims the benefit of priority under 35 USC § 119(e) of U.S. Provisional Patent Application No. 62/394,327 filed on Sep. 14, 2016. The contents of the above applications are all incorporated by reference as if fully set forth herein in their entirety.

FIELD AND BACKGROUND OF THE INVENTION

The present invention, in some embodiments thereof, relates to breast screening and, more particularly, but not exclusively, to a wearable device for automated screening of breast tissue.

US Publication Number US20100298895 A1 to Ghaffari et al. discloses "System, devices and methods are presented that integrate stretchable or flexible circuitry, including arrays of active devices for enhanced sensing, diagnostic, and therapeutic capabilities. The invention enables conformal sensing contact with tissues of interest, such as the inner wall of a lumen, a nerve bundle, or the surface of the heart. Such direct, conformal contact increases accuracy of measurement and delivery of therapy." (Abstract)

US Publication Number U.S. Pat. No. 6,620,115 B2 to Sarvazyan et al. discloses "A method and device in accordance with the present invention enabling detecting mechanical and structural properties of the breast tissue that are indicative of breast cancer. Detection of nodules is achieved by placing the breast into a mechanical scanning unit comprising of a two-dimensional pressure sensor array and a mobile linear pressure sensor array located opposite to the two-dimensional pressure sensor array, and analyzing the signals from the pressure sensors. The device is able to objectively detect presence of lesions suspicious for cancer or other breast pathologies in the breast and provide means for computerized three-dimensional mechanical imaging of the breast." (Abstract)

SUMMARY OF THE INVENTION

The following summary describes various aspects of devices and/or methods in accordance with some embodiments of the invention, and should not be construed as limiting.

According to an aspect of some embodiments of the invention, there is provided a wearable device for breast screening, comprising: at least one breast-contacting member shaped to contact a surface of a breast, the member comprising an array of force applying units and an array of sensors configured for sensing at least one parameter in response to force applied by the force applying units; the force applying units and the sensors disposed on or within the breast-contacting member and positioned to contact a surface of the breast; a memory storing one or more patterns to be applied by the force applying units, the patterns suitable to detect a lump underlying the surface; wherein the pattern comprises a sequence of forces that vary spatially and/or vary in time; a controller configured for reading data from the memory to automatically control application of force by at least some of the force applying units according to at least one of the patterns, the controller further configured for communicating with the array of sensors to receive signals associated with the at least one parameter sensed in response to the application of force, and to process the received signals to detect a lump.

In some embodiments, the breast contacting member is sized to contact at least 80% of the breast surface.

In some embodiments, the at least one parameter sensed by the sensors comprises pressure exerted by the breast onto the breast-contacting member in response to the applied force, and wherein at least some of the sensors comprise pressure sensors.

In some embodiments, the controller is configured to process the received signals by comparing one or more received signals of a certain tissue region to one or more signals received from surrounding tissue to detect a lump.

In some embodiments, the controller is configured to process the received signals by comparing one or more signals received from a certain tissue region to one or more signals received from the same tissue region when a different force pattern was applied.

In some embodiments, the pattern is selected to produce a response in the tissue that is indicative of existence of a lump.

In some embodiments, the force applying units comprise inflatable chambers, each chamber independently and controllably inflatable and deflatable, the chambers disposed within the member such that each chamber of the plurality of chambers has an elastic wall part configured to be in contact with a portion of the breast surface and to apply a known force to the portion when the chamber is inflated with an inflation fluid or air.

In some embodiments, the inflatable chambers are coupled to an inflation fluid source.

In some embodiments, the fluid is selected from, a gas, a mixture of gases, air, a soft gel and a liquid.

In some embodiments, a force applying unit comprises a moveable rod, a roller, or a bead.

In some embodiments, the force applying units are configured to apply force along a transverse plane, a sagittal plane and/or a coronal plane of a patient screened using the device.

In some embodiments, the controller is configured for processing the received signals to determine at least existence of a lump by comparing the signals to a reference table or to results of previous screenings of the patient.

In some embodiments, the controller is configured for processing the signals to determine borders of a lump.

In some embodiments, the controller is configured for processing the signals to determine a volume of a lump.

In some embodiments, the controller is configured for processing the signals to determine a degree of mobility of a lump.

In some embodiments, the controller is configured for processing the signals to determine a stiffness of a lump.

In some embodiments, the breast-contacting member is coupled to a fixating element configured for holding the member in contact with the breast.

In some embodiments, the fixating element is a strap configured to fit around the shoulder or around the back of the patient.

In some embodiments, the device is portable.

In some embodiments, the device is battery operated.

In some embodiments, the tissue contacting member is a cup like supporting member contoured to fit the shape of a breast.

In some embodiments, the cup like supporting member is shaped to counteract force applied by at least some of the units onto the tissue.

In some embodiments, the device is a bra comprising two cup-like supporting members.

In some embodiments, the controller comprises a communication module for communicating with an external system or database.

In some embodiments, at least one of: the force applying units and the sensors are configured to communicate with the controller via wireless communication.

In some embodiments, the device further comprises a chemical sensor attached to the member such that the chemical sensor is in contact with a nipple of the breast for obtaining information about one or more chemical constituents of a secretion discharged from the nipple.

In some embodiments, the device is configured to be self-operated by a patient using the device.

In some embodiments, the member is configured for shaping the breast into one of a plurality of base configurations.

In some embodiments, the controller is configured to select a screening protocol automatically according to a current shape of the breast.

In some embodiments, the member comprises at least one extension shaped and sized to contact a tissue region outside the breast area.

In some embodiments, the device comprises at least one extension shaped and sized for screening tissue of the axillary area.

In some embodiments, the extension is shaped and sized for contacting the axillary tail.

In some embodiments, the extension shaped and sized for contacting axilla tissue located directly under the joint.

In some embodiments, the controller is configured to map the received signals.

In some embodiments, the controller is configured to detect a location of a lump relative to the tissue surface or relative to the thoracic cage.

In some embodiments, a single array is configured for both applying force and for sensing force.

In some embodiments, the force applying unit and the sensor define a single unit.

In some embodiments, the device further comprises a removable membrane or pad shaped and sized to fit a surface of the breast-contacting member that engages the breast.

In some embodiments, the device comprises one or more cameras configured for acquiring an image of the breast.

According to an aspect of some embodiments of the invention, there is provided a method of screening breast tissue for early detection of cancer, comprising providing a wearable device contoured to fit the shape of a breast; automatically applying force to breast tissue using the device, the force applied in at least one pattern selected to detect a lump underlying a surface of the breast; the pattern comprising one or more forces that vary spatially and/or vary in time; automatically sensing a tissue response to the applying of force; and analyzing the received force-related signals to identify a lump in the breast.

In some embodiments, sensing comprises detecting pressure exerted by the tissue onto the device.

In some embodiments, the device comprises an array of force applying units and an array of sensors, and wherein the applying of force is performed via at least one of the force applying units and the sensing is performed via one or more sensors positioned adjacent the force applying unit.

In some embodiments, applying of force comprises pinching tissue between spaced apart units.

In some embodiments, applying of force comprises hooking of tissue.

In some embodiments, applying of force comprises pushing tissue in substantially straight lines or curved lines.

In some embodiments, applying of force comprises applying an advancing pressure wave.

In some embodiments, the pattern comprises a linear pattern, a non-linear pattern, a spiral pattern, a circular pattern, an arc-like pattern.

In some embodiments, at least two patterns are applied simultaneously, each pattern applied to a different tissue region.

In some embodiments, a tissue region comprises one of four quadrants of the breast.

In some embodiments, applying of force comprises compressing tissue towards the thoracic cage or compressing tissue in a cross-wise direction of the breast.

In some embodiments, analyzing comprises detecting variations in force exerted by the tissue onto the device in response to the applying of force.

In some embodiments, analyzing comprises assessing a profile of tissue resistance in response to the applied force.

In some embodiments, a rise of fall in the tissue resistance is indicative of a border between tissues of different consistencies.

In some embodiments, the method further comprises testing an identified lump to determine whether the lump is benign or malignant.

In some embodiments, applying force comprises gradually applying force effective to sense superficial, medium, and deep layers of the tissue.

In some embodiments, analyzing comprises applying a signal-processing algorithm to determine a location of a lump.

In some embodiments, the method further comprises, prior to applying of force, aligning the device to the breast of the screened patient.

In some embodiments, the method further comprises producing a pressure distribution map of the received pressure signals.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as a keyboard or mouse are optionally provided as well.

This Summary introduces a selection of concepts in a simplified form that are further described below in the Description of the Figures and the Detailed Description. This Summary is not intended to identify key features or essential features of the claimed subject matter, nor is it intended to be used to limit the scope of the claimed subject matter.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4A:
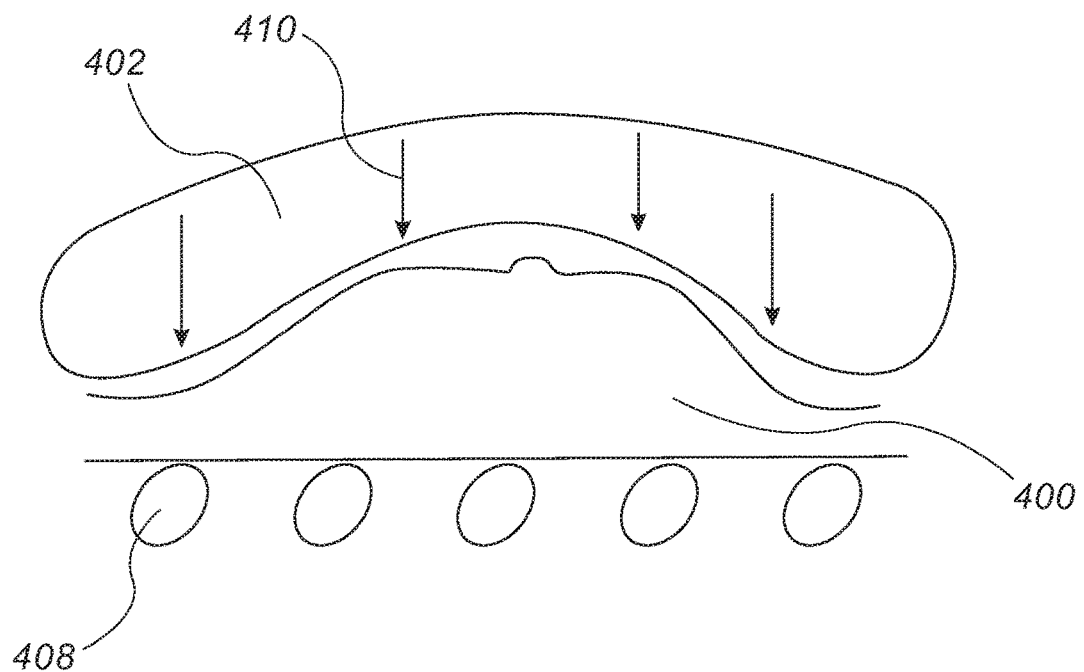
Figure 4B:
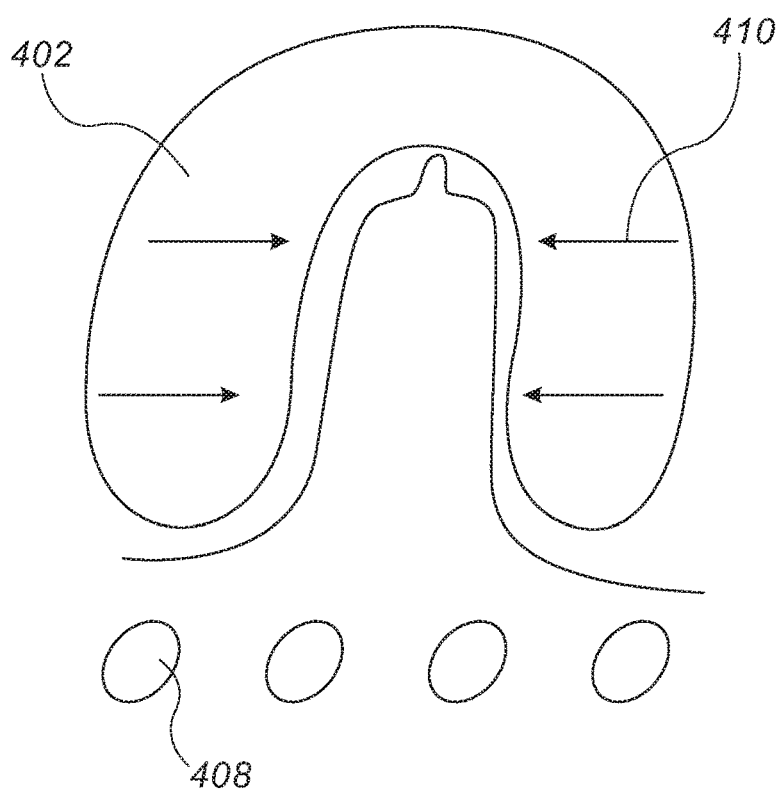
Figure 7:
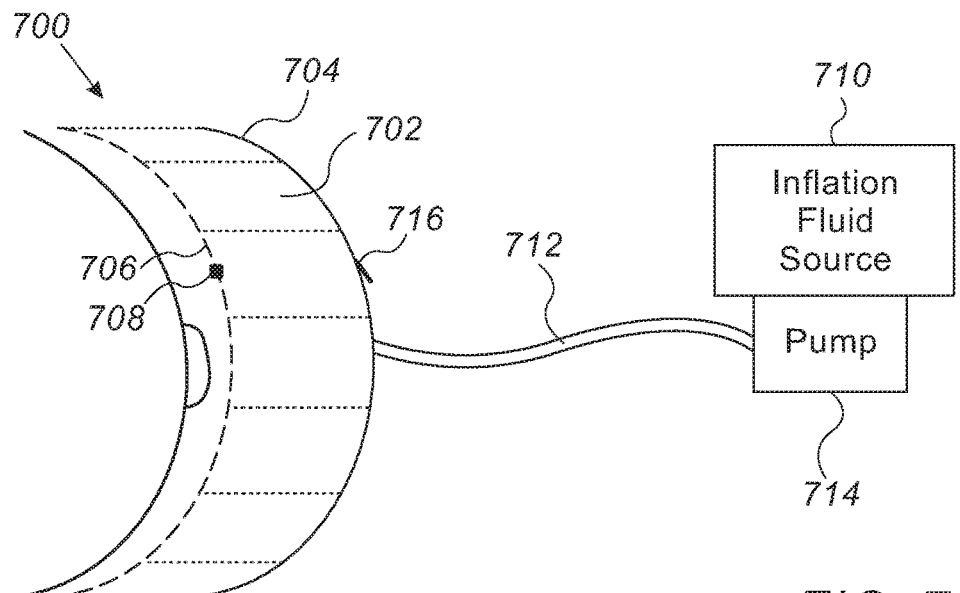
Figure 8A:
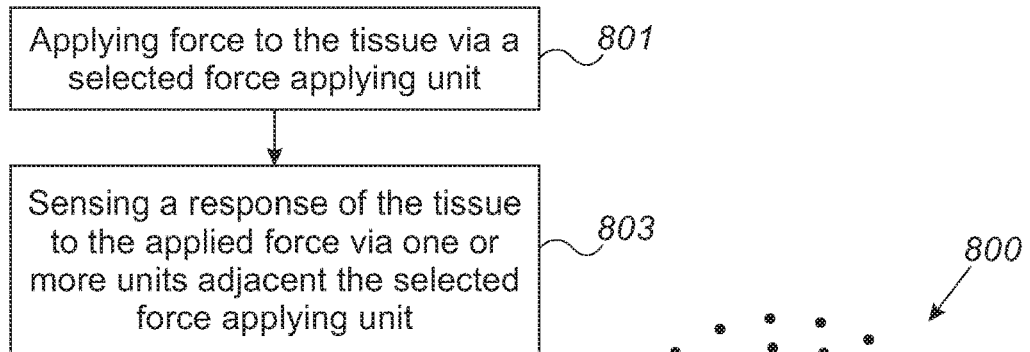
Figure 8B:
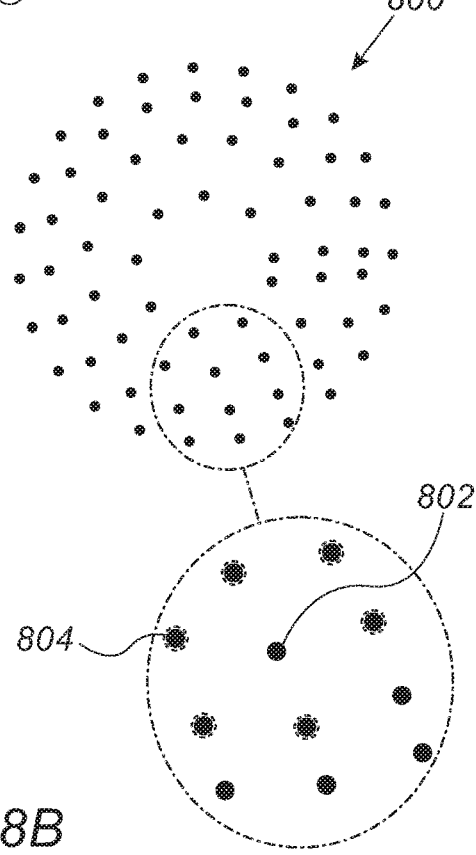
Figure 9:
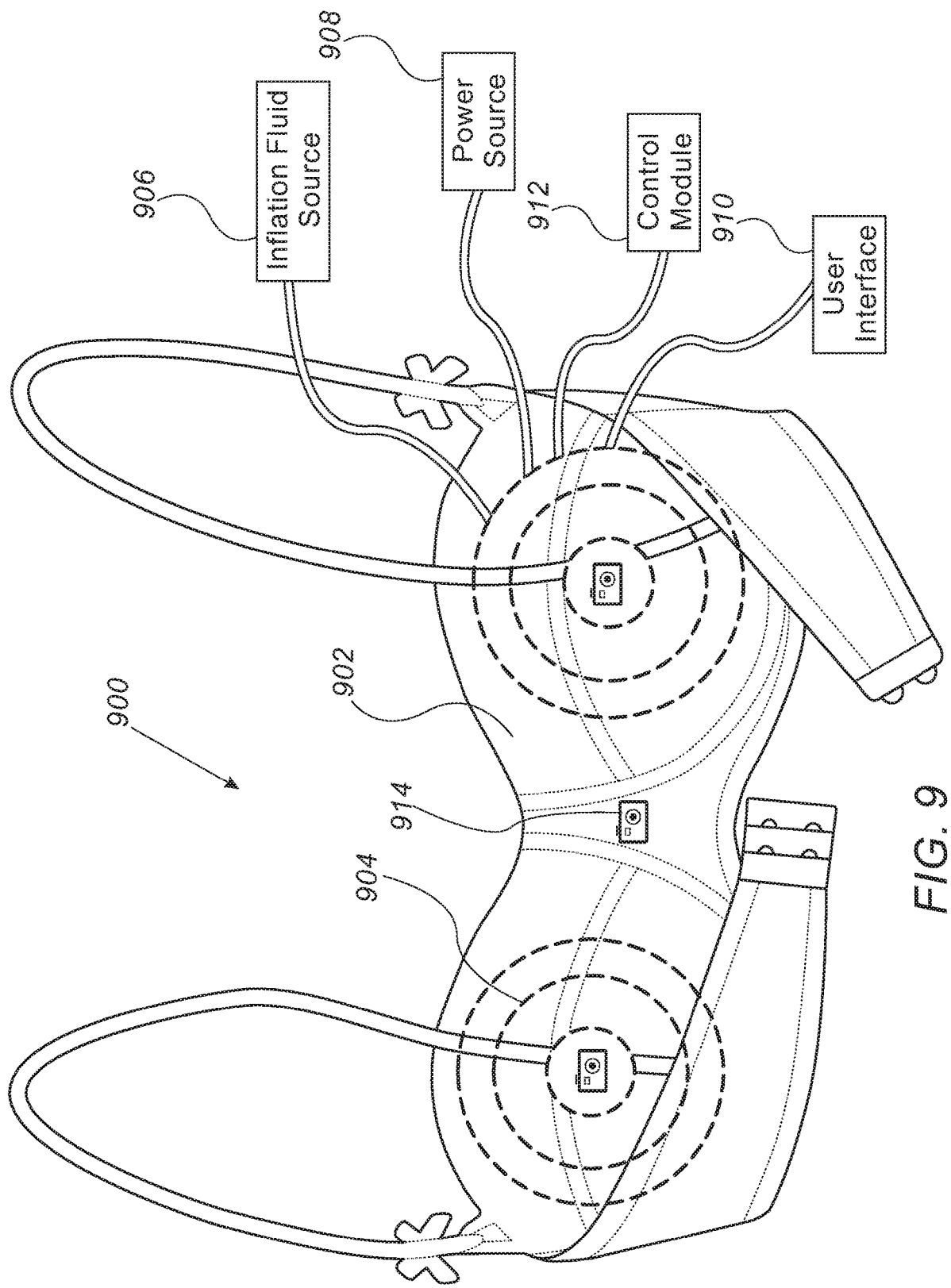
Figure 10A:
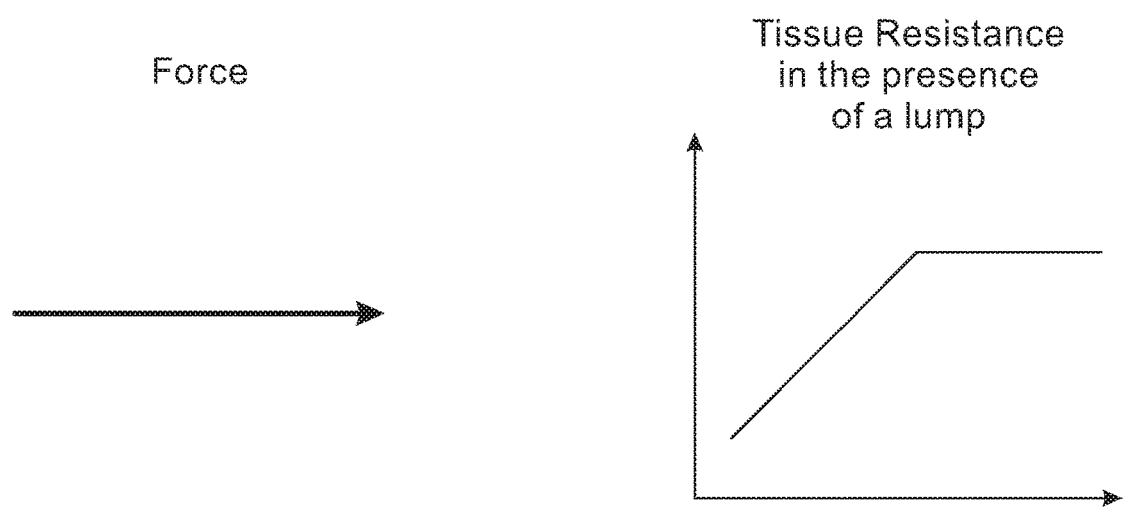
Figure 10B:
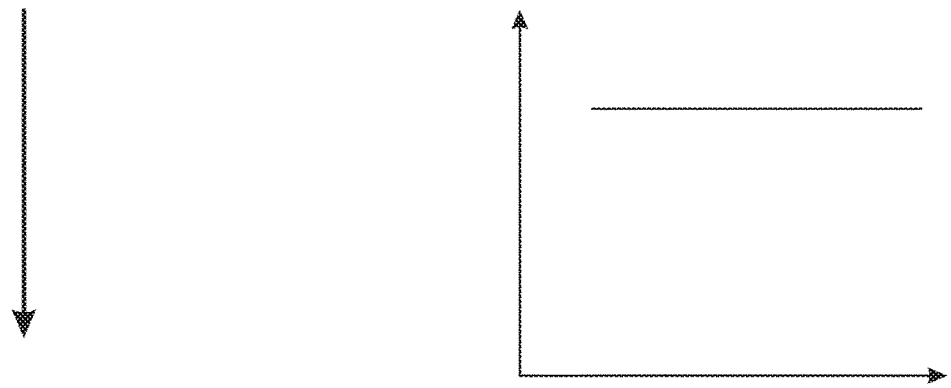
Figure 10C:
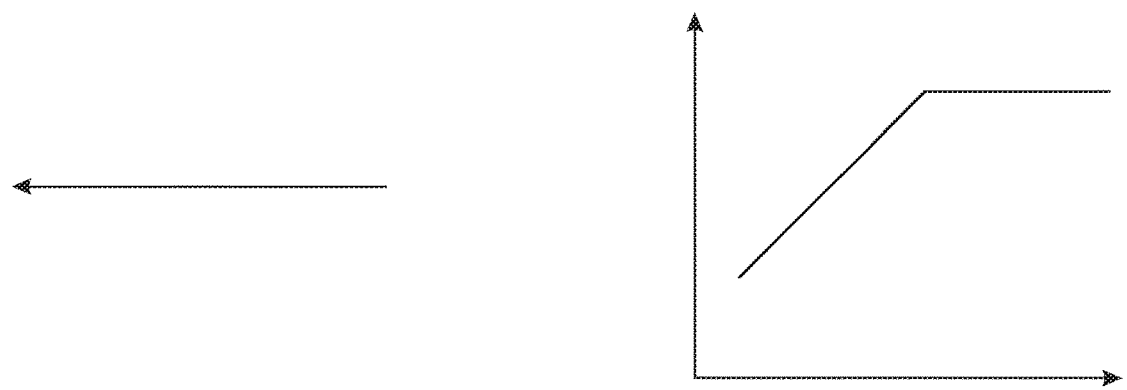
Figure 11A:
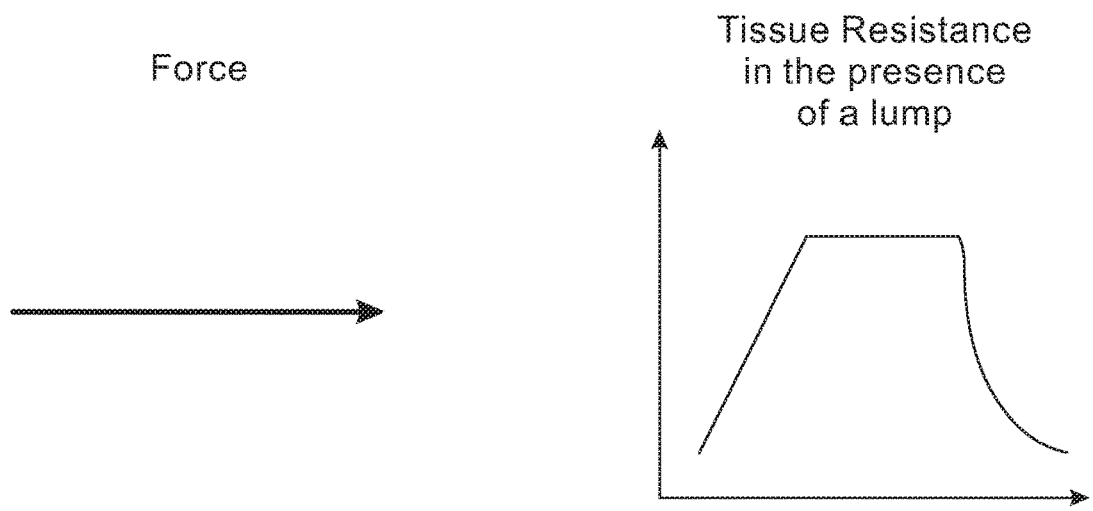
Figure 11B:
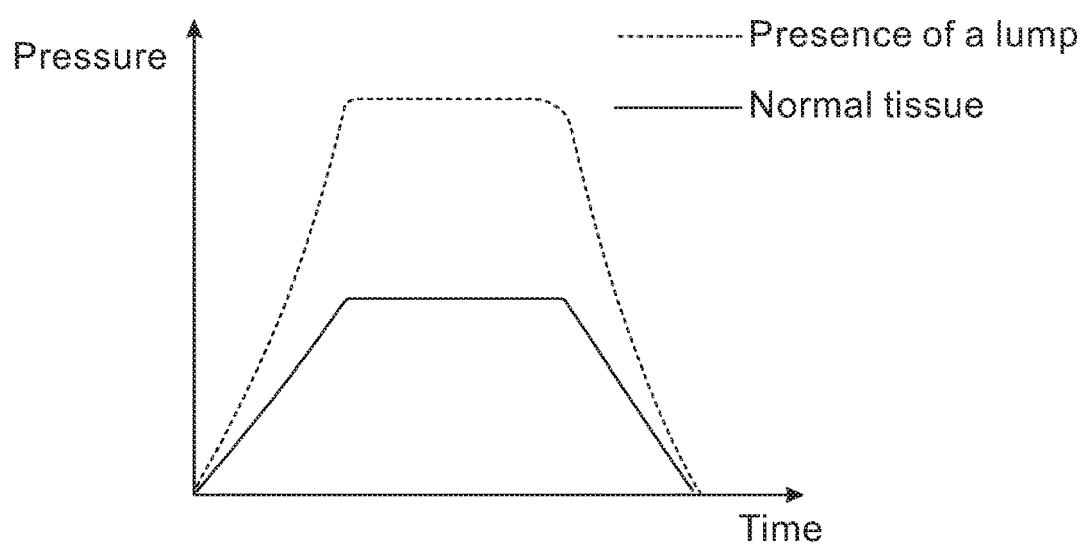
Figure 12:
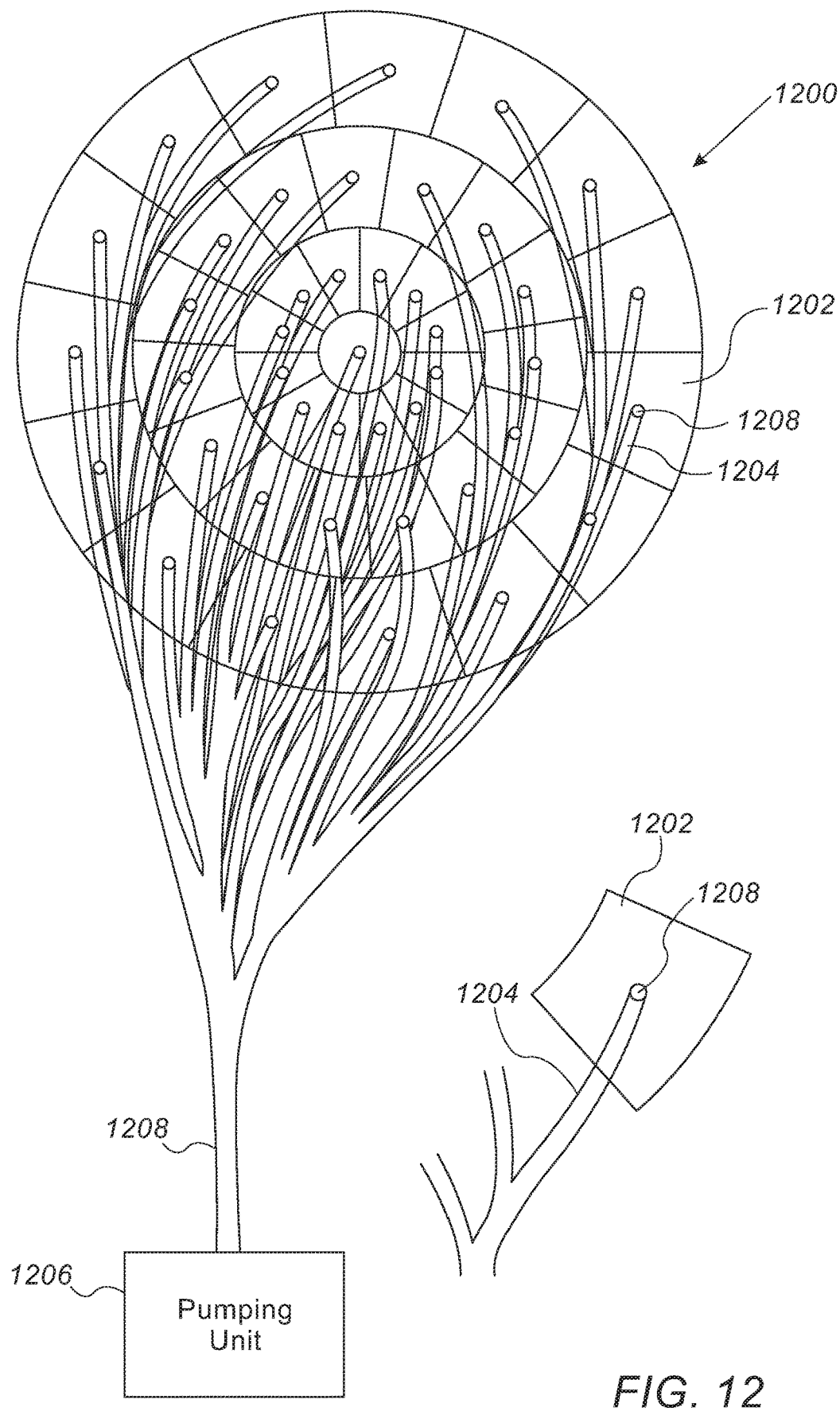
Figure 13:
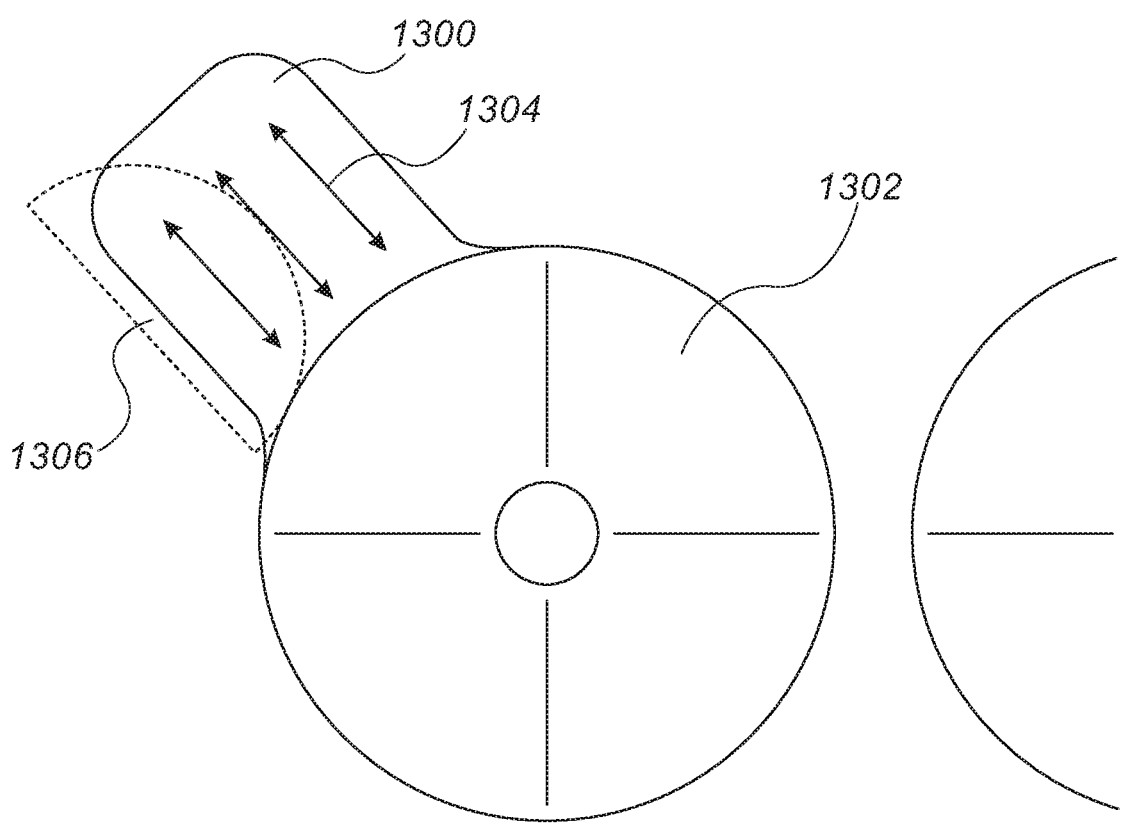
Figure 14A:
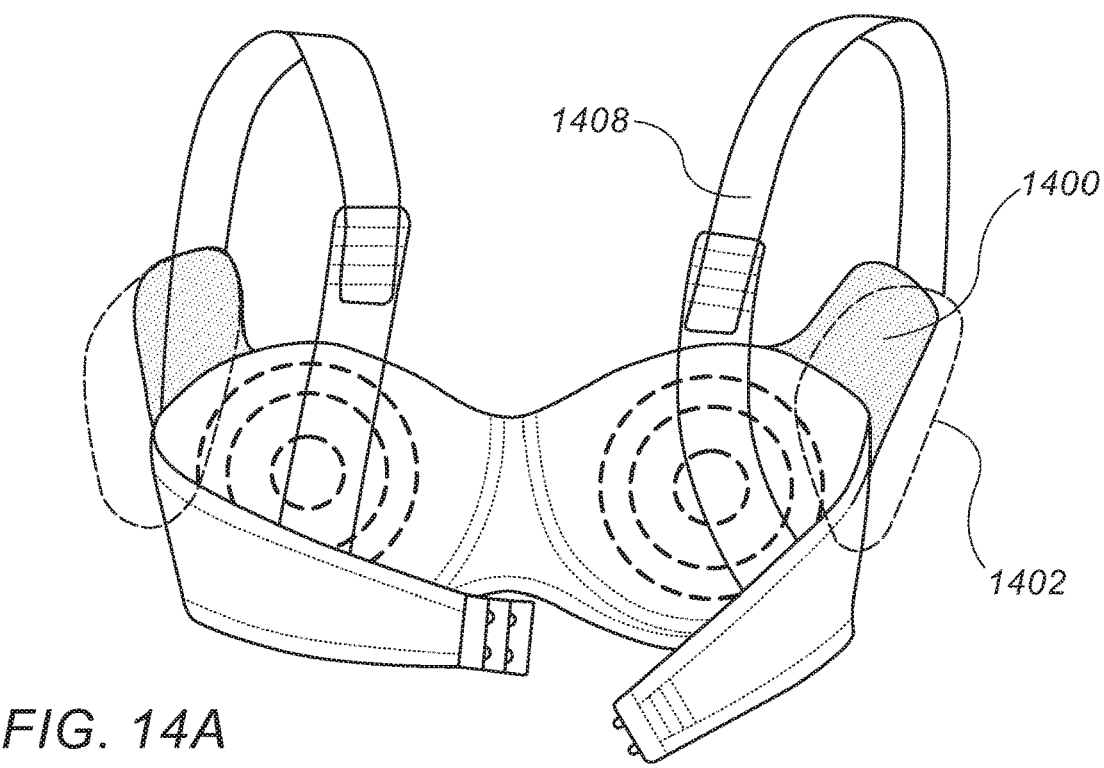
Figure 14B:
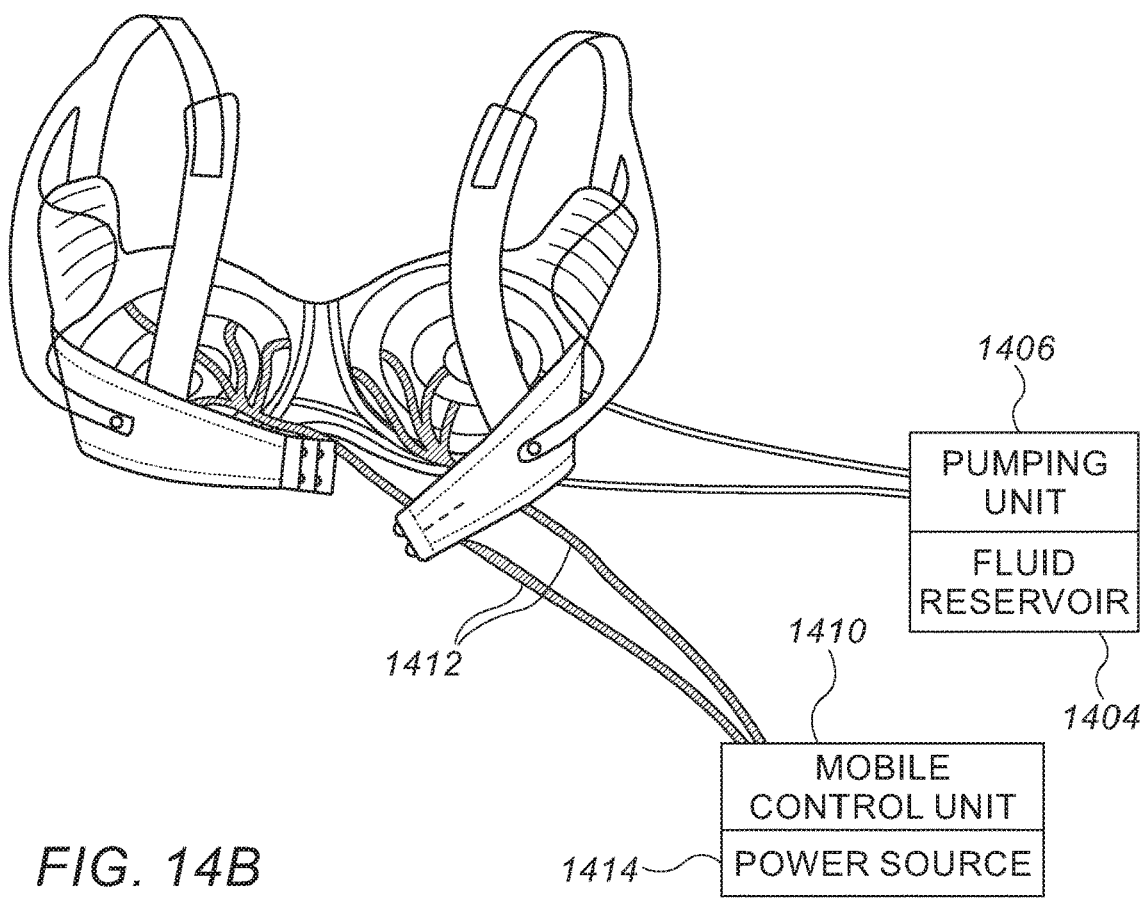
Figure 15B:
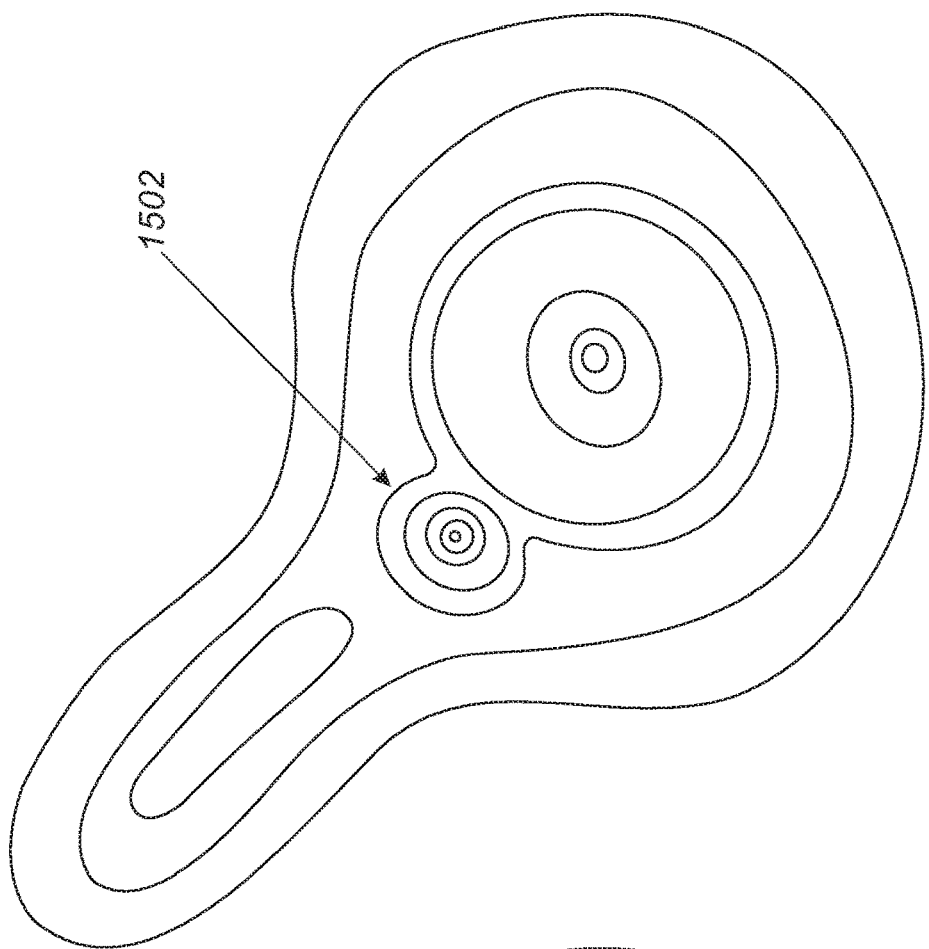
Figure 15A:
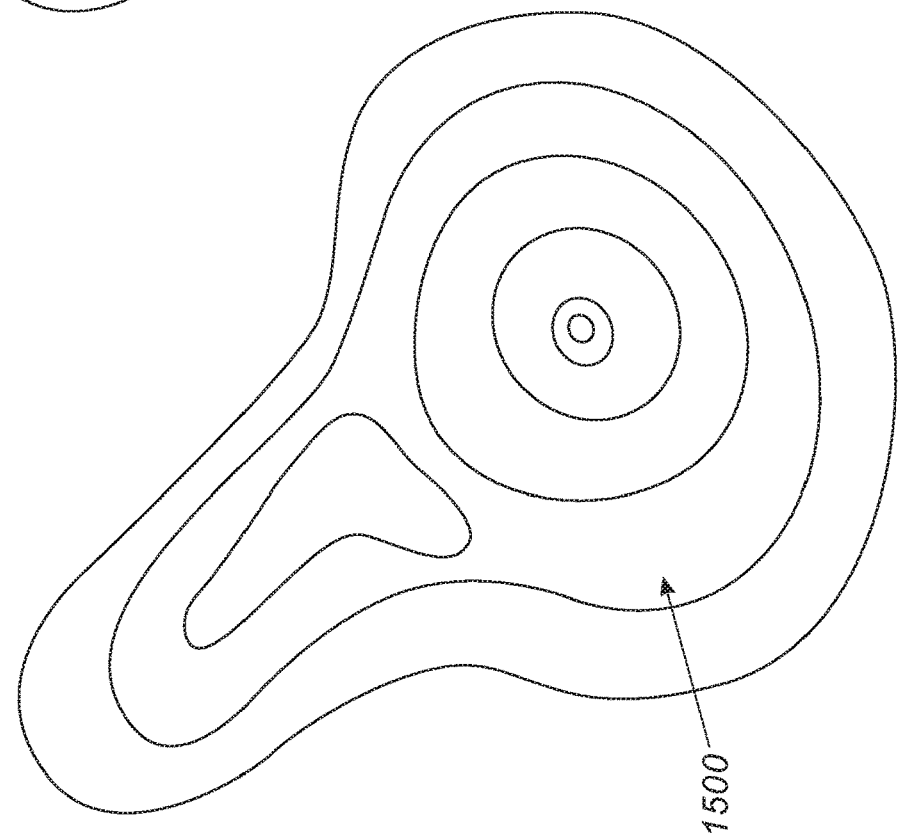

FIGS. 4A-B schematically illustrate shaping of the breast, according to some embodiments of the invention;

FIGS. 5A-E are exemplary spatial force patterns for applying onto breast tissue, according to some embodiments of the invention;

FIGS. 6A-D show various effects on the tissue in response to applying force at different directions and/or magnitudes, according to some embodiments of the invention;

FIG. 7 schematically illustrates a wearable screening device comprising a plurality of inflatable chambers, according to some embodiments of the invention;

FIGS. 8A-B are a flowchart (8A) and a schematic illustration (8B) of exemplary activation of an array of force applying and/or sensing units, according to some embodiments of the invention;

FIG. 9 shows a bra-shaped device for screening breast tissue, according to some embodiments of the invention;

FIGS. 10A-C are graphical representations of tissue resistance sensed in the presence of a lump in the tissue, according to some embodiments of the invention;

FIGS. 11A-B are other examples of graphical representations of tissue resistance sensed in the presence of a lump in the tissue, according to some embodiments of the invention;

FIG. 12 illustrates a supporting member comprising a plurality of inflatable chambers, according to some embodiments of the invention;

FIG. 13 is a schematic illustration of a device comprising an extension for screening the axillary tail, according to some embodiments of the invention;

FIGS. 14A-B are illustrations of bra shaped devices comprising axillary extensions, according to some embodiments of the invention; and FIGS. 15A-B are examples of pressure distribution maps of a normal breast (15A) and a breast exhibiting a lump (15B), according to some embodiments of the invention.

DESCRIPTION OF SPECIFIC EMBODIMENTS OF THE INVENTION

The present invention, in some embodiments thereof, relates to breast screening and, more particularly, but not exclusively, to a wearable device for automated screening of breast tissue. In some embodiments, the device is configured for early detection of lumps in the breast. In some embodiments, the device is configured for early detection of cancer.

An aspect of some embodiments relates to automatically applying force onto breast tissue in a pattern suitable for detecting a lump underlying the surface of the tissue. In some embodiments, the pattern imitates manual palpation of the breast, for example by applying forces having magnitudes and/or directions and/or spatial patterns selected in accordance with those applied by the physician's fingers. In some embodiments, the pattern is suitable to produce a response in the tissue that is indicative of existence of the lump. For example, force is applied to push tissue, compress tissue, pinch tissue, hook over tissue, and/or other actions suitable to differentiate between a lump and normal tissue. In an example, the pattern comprises applying an advancing pressure wave to the tissue. In some embodiments, the pattern is suitable to accentuate the lump's mobility characteristics and/or elasticity and/or other mechanical properties which may be different from corresponding properties of the surrounding normal tissue. In some embodiments, the applied forces vary in time and/or vary spatially.

An aspect of some embodiments relates to a wearable device configured for detecting a lump and/or other tissue irregularity by applying force onto breast tissue and sensing a response in the tissue. In some embodiments, sensing comprises collecting force-related signals in response to the applying of force, such as pressure exerted by the tissue onto the wearable device.

In some embodiments, the device comprises at least one breast-contacting member shaped and/or sized to contact most of the breast surface, for example at least 50%, at least 70%, at least 80%, at least 90% or intermediate, larger or smaller surface areas of the breast. Optionally, the breast contacting member contacts the skin surface and/or nipple, over fibrous and/or glandular tissue forming the breast. In some embodiments, the breast-contacting member comprises or is attached to a fixating element configured to hold the breast contacting member in contact with the breast. In some embodiments, the fixating element comprises a strap, band, an adhesive surface, a wearable garment and/or other element suitable for placing and/or maintaining the breast contacting member in contact with the breast surface.

In some embodiments, the breast contacting member comprises a cup-like supporting member contoured to fit the shape of a breast. Optionally, the device is in the form of a bra, comprising two cup-like supporting members.

In some embodiments, the device comprises one or more portions (e.g. extensions) shaped and/or sized for contacting a surface of the chest, the "tail" of the breast and/or axillary region and/or other tissue surfaces outside the breast area. In some embodiments, the device comprises an extension shaped and sized for screening the axillary region, including, for example, the arm pit and the axillary tail. Optionally, the extension is removably attached to the cup-like supporting member.

In some embodiments, the device comprises an array including a plurality of force applying and/or sensing units, arranged to contact the tissue surface. Optionally, the array is embedded and/or mounted on the inner lining of the cup-like supporting member, facing the tissue.

In some embodiments, the force applying and/or sensing units comprise independently controllable inflatable chambers that are filled with fluid to apply selected pressures onto the tissue. Additionally or alternatively, a force applying unit comprises a rod, roller, a bead and/or any other structure suitable for applying force to the tissue.

In some embodiments, the breast-contacting member is shaped and/or sized to counteract force applied by one or more of the force applying units. Optionally, the breast contacting member holds the tissue in place so that when force is applied to a portion of the tissue, resistance of the tissue to the applied force can be measured.

In some embodiments, the device is configured to sense pressure exerted by the tissue onto the cup-like member in response to the applying of force. In some embodiments, pressure is measured at one or more tissue locations adjacent a tissue location to which force was applied, e.g. by applying a force via one of the units and sensing pressure exerted on one or more adjacent units, in response to the applied force. Optionally, at least some units of the array comprise a pressure sensor positioned to sense the pressure exerted by the tissue.

In some embodiments, the received signals are analyzed to identify existence of the lump or properties thereof. Optionally, analyzing is performed by applying signal processing algorithms such as data segmentation to detect existence of the lump and/or the lump borders. In some embodiments, analyzing is performed to determine properties of the lump, such as volume, spatial location, depth (e.g. relative to the tissue surface and/or relative to the thoracic cage), dimensions, elasticity, mobility and/or other properties. In some embodiments, a firmness different than the surrounding tissue is indicative of a benign space occupying lesion, a malignant lump and/or other types of suspicious mass. In some embodiments, irregular borders are indicative of a malignant lump. In some embodiments, limited mobility (e.g. a lump that is hard to push and/or one that adheres to adjacent tissue) is indicative of a malignant lump. In some embodiments, a sudden rise or fall in the resistance of the tissue to the applied force is indicative of a border between tissues of different consistencies or types.

In some embodiments, analyzing is performed by comparing signals received from a predefined tissue region to signals received from one or more tissue regions in a vicinity of the predefined tissue region. Additionally or alternatively, analyzing is performed by comparing signals received from a predefined tissue region to previous measurements obtained from that tissue region.

In some embodiments, screening results are compared to previous screening results obtained using the device. Optionally, discrepancies between the compared screening results are indicative of a lump. Additionally or alternatively, screening results obtained using the automatic device are compared to screening results obtained using other screening modalities and/or to manual screening.

In some embodiments, a coordinate system is defined for the array of force applying and/or sensing units. Optionally, tissue movement in response to the applying of force is defined according to the coordinate system. Optionally, a location of a suspected lump is defined according to the coordinate system. In some embodiments, a three dimensional Cartesian coordinate system is used. In an example, the Z axis indicates a depth relative to the breast tissue surface and/or relative to the thoracic cage, and the X and Y axes indicate a spatial location on the tissue surface.

In some embodiments, the device is configured to shape the breast with respect to the cup-like support member and/or with respect to the thoracic cage so as to apply force to different tissue regions of the breast and/or to reach deeper tissue layers. In some embodiments, shaping of the breast comprises moving tissue to cause a lump underlying the tissue surface to move away from surrounding tissue, for example to separate the lump from its surrounding tissue to assess existence and/or properties of the lump.

In some embodiments, the device is configured to operate according to a predetermined protocol, for example a protocol suitable to detect certain types of tissue irregularities and/or a protocol suitable for screening one or more types of tissue (e.g. lymph nodes) and/or a protocol suitable for screening a breast of a certain volume or volume range. Optionally, the device is configured to sense a volume and/or one or more dimensions of the breast and to determine and/or modify the protocol accordingly. In some embodiments, the device is configured to operate according to a plurality of protocols, for example protocols involving applying of force to the tissue in multiple predefined patterns, one after another or simultaneously (e.g. by applying different force patterns to different regions of the breast).

In some embodiments, the device comprises one or more sensors for obtaining additional information for assessing the tissue, such as a chemical sensor configured to contact the nipple for obtaining information about one or more chemical constituents of a secretion discharged from the nipple.

In some embodiments, the device is configured to be self-operated by a patient using the device. Optionally, the device is a hand-held device. In some embodiments, the device is portable.

In some embodiments, the device is configured to perform a visual inspection of the breast, for example by comprising one or more cameras configured for acquiring an image of the breast. Optionally, an image is acquired before and/or after screening. In some embodiments, the image is processed for determining visual properties of the tissue which may be associated with existence of a lump, for example asymmetry of the tissue, skin color differences, hematomas and/or other visual properties.

A lump as referred to herein may include a tissue mass, clamp or aggregation having one or more different properties than surrounding tissue, such as different elasticity, mobility and/or resilience properties; a tissue mass having an irregular shape; a tissue mass having one or more borders, optionally irregular; a pushable or otherwise movable or pinchable tissue mass.

Before explaining at least one embodiment of the invention in detail, it is to be understood that the invention is not necessarily limited in its application to the details of construction and the arrangement of the components and/or methods set forth in the following description and/or illustrated in the drawings and/or the Examples.

The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
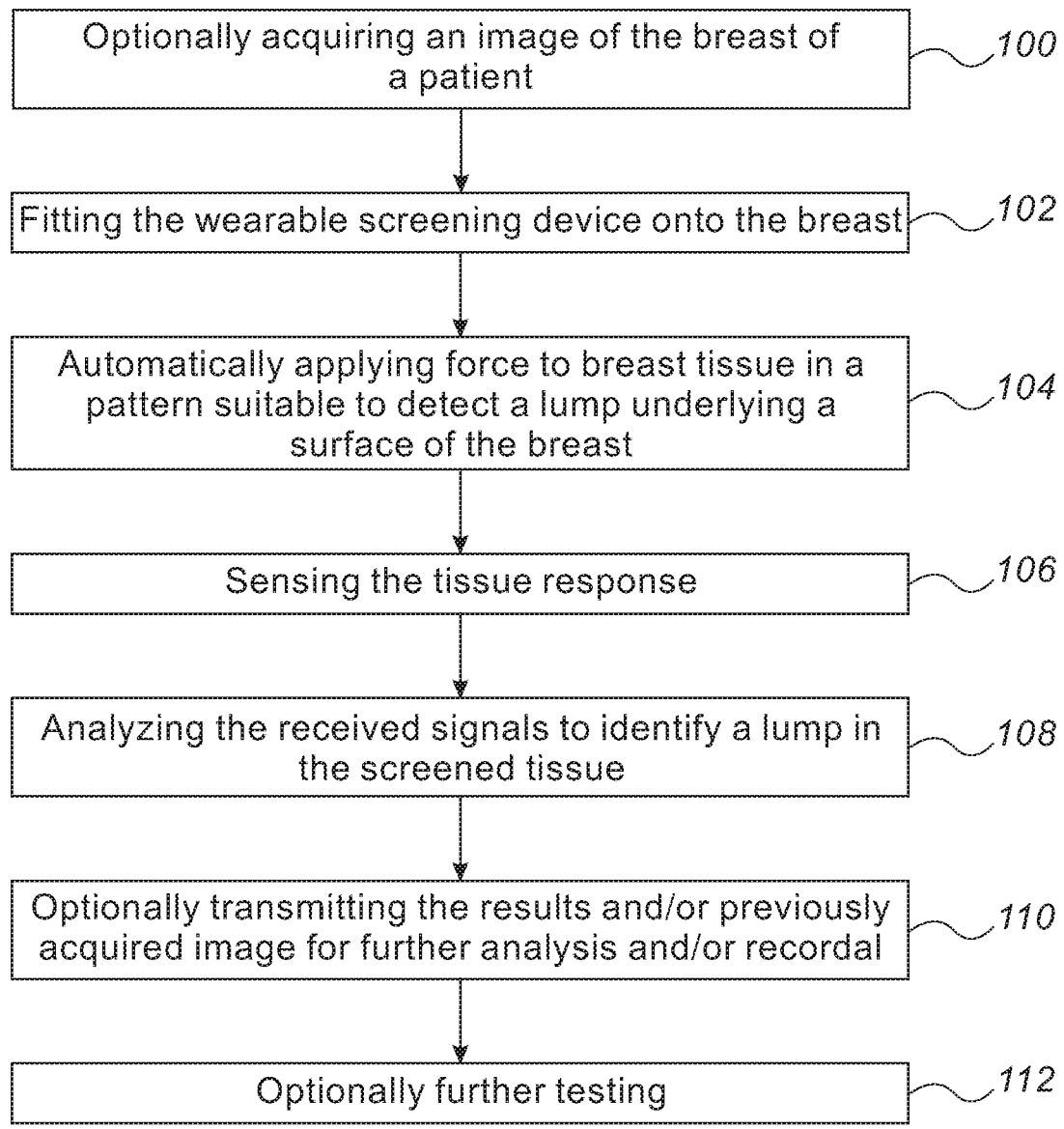
FIG. 1 is a flowchart of a method for automatic screening of breast tissue using a wearable device, according to some embodiments of the invention.

Referring now to the drawings, FIG. 1 is a flowchart of a method for automatic screening of breast tissue to detect a lump underlying a surface of the breast, according to some embodiments.

In some embodiments, an image of the breast is acquired prior to the screening (100). In some embodiments, the image is acquired via a camera and/or other optical instruments configured for capturing an image of the breast. Optionally, the camera is incorporated in the wearable screening device. Optionally, when taking the image of the breast, the device is held in front of the patient such that it is leveled with the breast.

In some embodiments, the screening device is fitted onto the breast of a patient (102). In some embodiments, the device comprises one or two cup-like supporting members contoured to fit the shape of a breast. Optionally, the device is in the form of a bra. In some embodiments, fitting comprises shaping the device and/or the breast with respect to each other and/or with respect to the thoracic cage. In some embodiments, fitting comprises obtaining contact between at least a portion of the device and at least a portion of the examined breast.

In some embodiments, screening is performed by automatically applying force onto the tissue (104), and sensing the tissue response (106). In some embodiments, the tissue response is sensed by measuring force exerted by the tissue onto the device simultaneously and/or immediately following the applying of force. In some embodiments, force is applied in a pattern suitable to detect a lump underlying a surface of the breast. The pattern may be suitable to detect other tissue irregularities, such as cysts, scars, fibrotic areas, swollen or edematous areas, retracted areas.

In some embodiments, the pattern comprises a spatially varying force. In some embodiments, the pattern comprises a time-varying force.

In some embodiments, the pattern imitates manual palpation of the breast, for example simulating the amount of force applied by the physician's fingers onto the breast and/or simulating palpating movements (or portions thereof) performed by the physician.

In some embodiments, the applied force is increased gradually, for example so as to effectively palpate superficial, medium, and/or deep layers of the tissue.

In some embodiments, the pattern is suitable to produce a response in the tissue that is indicative of existence of a lump. For example, force is applied to push tissue, compress tissue, hook over tissue, and/or other actions suitable to differentiate between a lump and normal tissue. In some embodiments, the pattern is selected to accentuate the lump's mobility characteristics and/or elasticity and/or other mechanical properties which may be different from corresponding properties of the surrounding normal tissue, thereby contributing to detection of the lump.

In some embodiments, force is applied in a substantially perpendicular direction to the thoracic cage to compress breast tissue against the underlying thoracic cage. Additionally or alternatively, force is applied from diametrically opposing directions of the cup-like supporting member, on one or more planes substantially parallel to the thoracic cage.

In some embodiments, local force applied for example by a single unit is applied for a time period of between 1 sec to 10 seconds, such as 0.5 second, 1 second, 7 seconds or intermediate, longer or shorter time periods. The response in the tissue may be immediate and/or occur with some delay from the applying of force.

Optionally, the device is configured to sense signals immediately following applying of force and/or a time period after applying of force.

In some embodiments, the received signals are analyzed to identify a lump and/or other tissue irregularity in the screened tissue (108). In some embodiments, the received signals are analyzed to detect existence of a lump. Optionally, the signals are analyzed to detect properties of the lump, such as volume, spatial location, dimensions, elasticity, regularity of the lump's borders and/or other properties. In some embodiments, one or more signal processing algorithms are applied to the received signals. Optionally, data segmentation is performed to detect the lump and/or identify borders of the lump.

In some embodiments, an intensity of a received signal is compared to one or more surrounding background signals, for example to an averaged intensity of the background signals.

In some embodiments, an intensity of a received signal is compared to an expected intensity, for example an intensity expected for certain regions of the breast (for example the breast periphery, the breast center) and/or an intensity expected in accordance with breast volume and/or size and/or an intensity expected for a certain medical condition.

In some embodiments, a map of the pressure distribution in the breast is produced based on the received signals. In some embodiments, the map comprises isobars (optionally in the form of colored lines) representing pressure applied by the tissue onto the device and sensed by the device.

In some embodiments, pressure sensed by a selected sensing unit over time is analyzed. The change in locally-sensed pressure may be indicative of tissue characteristics, type and/or content.

In some embodiments, spatial variations in the received signals in response to the applied force are detected. Optionally, signals received from a certain tissue portion that exhibit different properties (e.g. higher or lower pressure levels) as compared to signals received from surrounding tissue are indicative of a lump in that tissue portion.

In some embodiments, the received signals are compared to one or more previous measurements of the patient. Additionally or alternatively, the received signals are compared to a look up table or database including data collected from a plurality of patients, to determine a likelihood of existence of a lump in view of a diagnosis associated with the data collected from the plurality of patients.

In some embodiments, analysis of the received signals is designed to differentiate between a benign lump and a malignant lump. Optionally, differentiation is performed in accordance with tissue characteristics such as lump smoothness, regularity, and/or mobility (for example, a benign lump tends to be smoother than a malignant lump).

In some embodiments, screening results and/or an acquired image of the breast are transferred for further analysis and/or recordal. For example, in some embodiments, the results are transferred to a physician and/or medical center and/or an analysis center. In some embodiments, the results are transmitted to a database.

In some embodiments, the image is analyzed to deduce information about the tissue, for example information which is otherwise commonly obtained by a physician's visual examination. Such information may include, for example: asymmetry of the tissue, color changes or discolorations in the tissue, visible lumps, retraction of skin and/or nipple, swelling of skin, edematous skin, hematomas and/or other information that can be deduced from the acquired image. In some embodiments, image processing algorithms are applied for automatically deducing information from the image.

In some embodiments, the lump and/or a suspected tissue portion are further tested (112), for example by collecting a biopsy to assess malignancy, performing surgery, using ultrasound and/or mammography. In some cases, the lump is indicative of a cyst, neoplasm, a tumor, and/or other abnormal tissue growth. In cases in which one or more lumps are identified, the patient may be referred to further screening and/or testing.

In some embodiments, the device comprises an extension shaped and sized for screening the axillary region, including, for example, the axilla and breast tail.

Optionally, the extension is configured to be strapped onto the patient's shoulder. In some embodiments, the patient is instructed to raise their arm (e.g. to rest the arm above the head) to ensure contact between the extension and the tissue. In some embodiments, screening of the breast tail and/or axilla by the device is performed to detect primary lesions at the breast tail and/or enlarged, optionally metastatic lymph nodes in the axilla. Optionally, a force pattern applied by the axillary extension onto the tissue comprises force applied from the apex of the axilla and downwards in a distal direction, causing enlarged lymph nodes to pop-up in response to the applied force to facilitate their detection.

Figure 2:
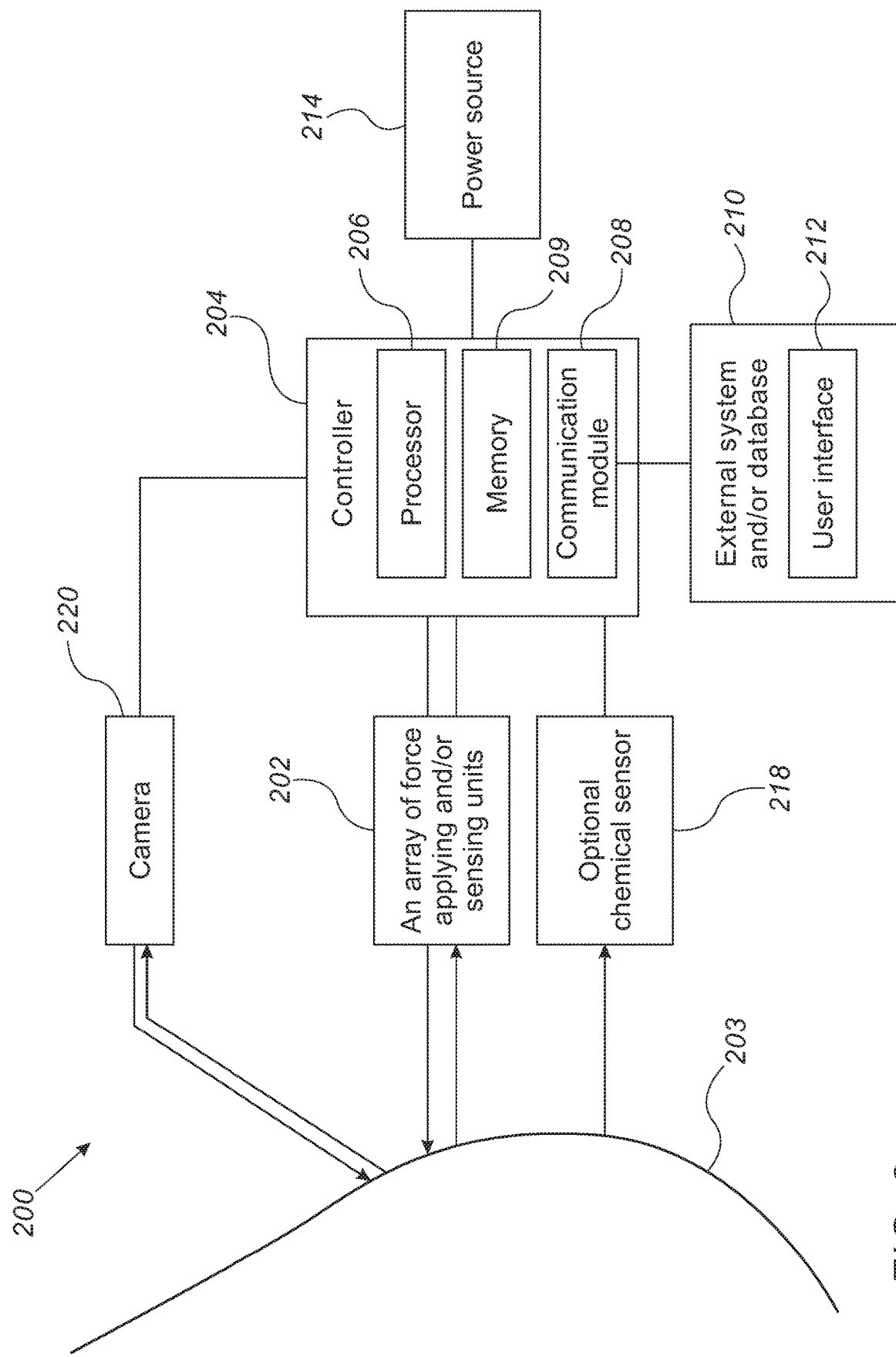
FIG. 2 is a block diagram of a system for automatic screening of breast tissue using a wearable device, according to some embodiments of the invention.

FIG. 2 is a block diagram of a system for automatic screening of breast tissue using a wearable device, according to some embodiments of the invention.

In some embodiments, system 200 comprises an array of a plurality of force applying and/or sensing units 202. In some embodiments, the array of units is embedded within and/or mounted on inner surface of a cup like supporting member (not shown herein), configured to fit onto the breast 203.

In some embodiments, the array comprises one or more force applying units and one or more sensing units (e.g. pressure sensing units). Optionally, a unit is configured to function both as a force applying unit and as sensing unit, for example by comprising a structure suitable for applying force onto the tissue and a sensor (e.g. pressure sensor).

In some embodiments, a force applying unit comprises an inflatable chamber, which can be filled with fluid (e.g. air) to apply pressure onto the tissue. Additionally or alternatively, a force applying unit comprises a rod or plunger, configured to project away from the supporting member in the direction of the tissue and to retract back into the supporting member. Additionally or alternatively, a force applying unit comprises a roller, a bead, and/or any other structure suitable for exerting force onto the tissue.

In some embodiments, a shape and/or size of a tissue contacting surface of the force applying unit is selected and/or modified to apply a certain pressure onto the tissue. For example, for the same amount of force, the force applying unit may comprise a pointy distal end face for applying relatively high, localized pressure, or a wide, flattened distal end face for applying lower pressure to a larger tissue surface region.

In some embodiments, a sensing unit comprises a pressure sensor (e.g. a membrane based pressure sensor, an electromechanical pressure sensor). In some embodiments, optical sensing is employed, and a sensing unit may be configured for receiving an optical signal. Additionally or alternatively, the sensing unit may be configured for receiving a chemical and/or electrical and/or magnetical and/or thermal signal.

In an exemplary embodiment, a force applying and/or sensing unit comprises an inflatable chamber that can be filled with fluid (e.g. air) to apply a selected pressure onto the tissue. Optionally, pressure exerted by the tissue onto the inflated chamber in response to the applying of force (e.g. force previously applied by the same unit and/or force previously or simultaneously applied by neighboring units) is sensed by detecting changes in the inflation level of the chamber and/or detecting deformation of the tissue contacting surface of the chamber. Optionally, the applied pressure is between 1 N/cm^2 to 100 N/cm^2, such as 3 N/cm^2, 10 N/cm^2, 70 N/cm^2 or intermediate higher or lower pressure.

In some embodiments, system 200 comprises a controller 204. In some embodiments, controller 204 is configured to control actuation of the array of units 202 to apply force according to a selected pattern or protocol.

Optionally, commands from controller 204 are transferred to array 202 via wired or wireless communication means.

In some embodiments, each of the force applying units is individually controlled. Optionally, a plurality of units are actuated simultaneously and/or successively to apply force according to a selected pattern. In an example, a single unit (e.g. a roller) and/or a plurality of units (e.g. a plurality of rods) are actuated to create an advancing pressure wave.

In some embodiments, controller 204 is configured to change assignment of a unit to act as a force applying unit or as a sensing unit. Optionally, a force applying unit is moved with respect to the tissue (e.g. projected outwardly to compress the tissue), while a sensing unit remains static. In some embodiments, each of the units comprises both a force applying element (e.g. rod, roller, extendible protrusion) and a sensing element (e.g. pressure sensor, optionally mounted on a tissue engaging end of the unit).

In some embodiments, controller 204 comprises or is in communication with a processor 206. In some embodiments, processor 206 is configured for processing the received signals to determine presence of a lump in the tissue. Optionally, processor 206 is configured for determining one or more lump properties, such as: borders of the lump, dimensions of the lump, specific location of the lump (e.g. by setting coordinates corresponding to the array of units), a degree of mobility of the lump, a level of stiffness of the lump, and/or other properties of the lump.

In some embodiments, controller 204 comprises and/or is in communication with a memory 209. In some embodiments, memory 209 stores a plurality of patterns applied by the device. Optionally, data concerning a pattern includes one or more of timing of applying of force, intensity profile, spatial distribution of the force and/or other operational parameters. In some embodiments, data concerning a pattern includes considerations for when analyzing signals received in response to the applied data.

In some embodiments, controller 204 comprises a communication module 208, configured to communicate via wired and/or wireless communication with an external system and/or database 210. In some embodiments, external system 210 comprises a laptop, a cellular phone, a computer, a hospital system. In some embodiments, external system comprises a user interface 212, for example comprising a screen for presenting the screening results to the patient and/or physician, and an input device for receiving data and/or instructions from the user and/or physician.

In some embodiments, processor 206 is configured to analyze the received signals and to map the distribution of pressure exerted by the tissue onto the cup-like member. In some embodiments, processor 206 is configured to assess the pressure exerted (or lack thereof) onto each of the sensing units of the array. Optionally, the pressure distribution map is then presented to the physician via user interface 212.

Additionally or alternatively, a visual and/or audible and/or tactile alert are provided to the physician and/or patient via user interface 212 in response to an indication obtained by processor 206.

In some embodiments, an indication of a location of a detected lump can be observed from the mapped pressure distribution. Additionally or alternatively, an indication of a location of a detected lump is provided by the lump's relative distance from a reference point, such as the center of the nipple.

In some embodiments, system 200 comprises a power source 214. In some embodiments, power source 214 comprises a battery, optionally rechargeable.

Additionally or alternatively, system 200 is powered by mains electricity.

In some embodiments, system 200 is configured to automatically screen the tissue once activated, for example once the patient or physician (and/or other clinical personnel) turn an on/off switch. A potential advantage of a fully automated system may include providing for self-screening by a patient, with minimal or no intervention by a technician, physician or other specialist.

In some embodiments, system 200 comprises one or more sensors for collecting data other than force-related data from the tissue. In some embodiments, system 200 comprises one or more chemical sensors 218 configured to detect and, in some embodiments, assess chemical constituents of a secretion discharged from the nipple.

In some embodiments, controller 204 is configured to store the recorded data.

Additionally or alternatively, the recorded data is transferred (e.g. via communication module 208) to external storage, e.g. network or cloud storage.

In some embodiments, system 200 is configured to adjust the applied force in response to an indication from the patient. For example, if the applied force is too high and may become painful for the patient, the device may be configured to reduce the applied force upon receiving the indication from the patient via user interface 212.

Optionally, a safety mechanism is provided, enabling the patient to modify and/or terminate screening.

In some embodiments, system 200 comprises one or more cameras 220 configured for acquiring an image of the breast, such as a high-definition (HG) image.

Optionally, a camera is positioned at a respective center of the device, for example embedded in between the two cups. Additionally or alternatively, a camera is positioned at one or both cups, for example embedded at a center of the cup.

In some embodiments, one or more images of the breast (acquired, for example, before and/or after screening) are communicated to controller 204.

Optionally, the images are analyzed for assessment of visual tissue properties that may be associated with existence of a lump, such as asymmetry, color differences, and/or others.

Figure 3:
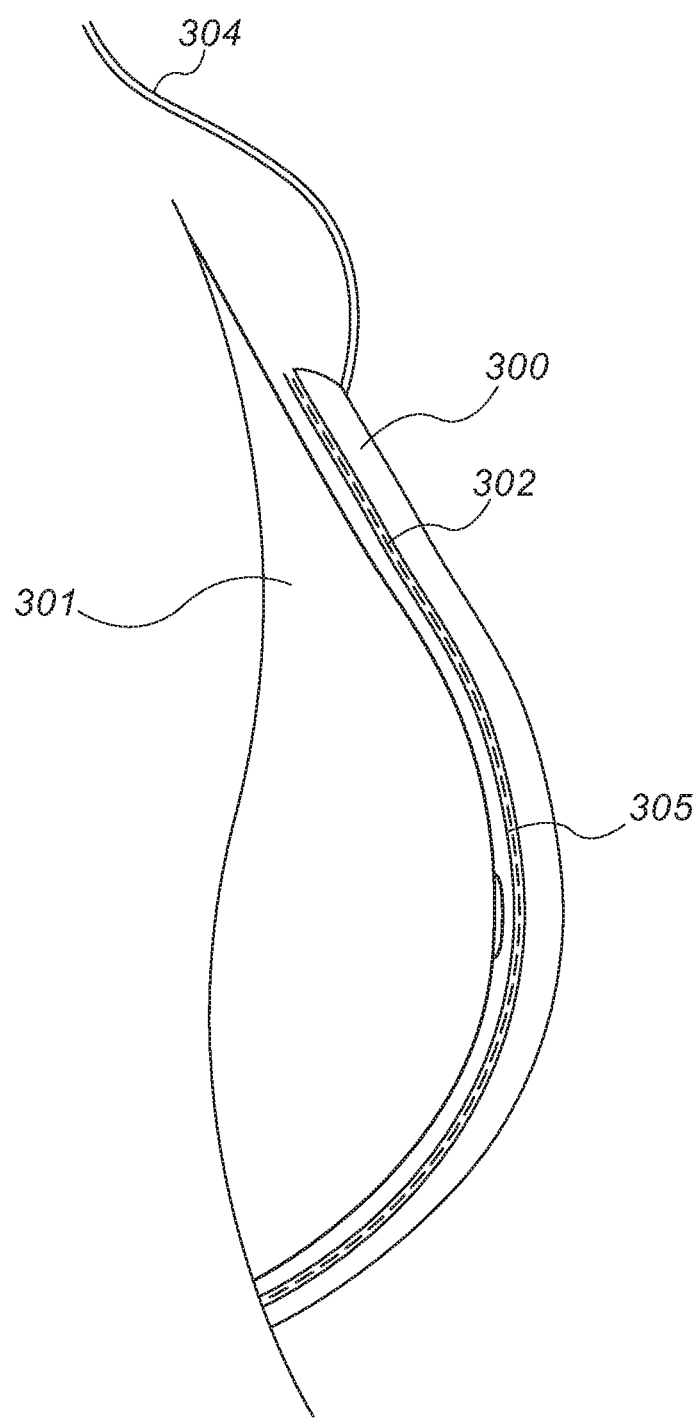
FIG. 3 is a schematic side view of a cup-like supporting member configured for applying force to breast tissue, according to some embodiments of the invention.

FIG. 3 is a schematic side view of a cup-like supporting member 300 configured for applying force to breast tissue, according to some embodiments of the invention.

In some embodiments, supporting member 300 is contoured to fit the breast 301, for example comprising a rounded (e.g. dome like) profile.

In some embodiments, an array of force applying and/or receiving units 302 is embedded within supporting member 300. Additionally or alternatively, the array is mounted or printed on an inner lining of the supporting member 300.

Additionally or alternatively, the array is arranged on a stretchable mesh. Optionally, the stretchable mesh is adjustably fitted to an inner lining of supporting member 300 or any other garment suitable to hold the mesh to the breast.

In some embodiments, units 302 are arranged to substantially surround the tissue surface. In some embodiments, force is applied along a transverse plane, a sagittal plane, a coronal plane and/or any intersecting planes of a patient screened using the device.

In some embodiments, supporting member is elastic. Optionally, supporting member 300 is flexible enough to provide for fitting the member onto the breast such that contact is formed between array 302 and the surface of the tissue (supporting member 300 is shown spaced apart from the tissue for clarity purposes).

In some embodiments, supporting members of various dimensions are provided, for fitting different breast anatomies.

In some embodiments, one or more fixating elements such as a strap 304 is attached to the cup-like supporting member for holding the supporting member in contact with the breast. Optionally, the fixating element is configured to extend above the shoulder, around the back and/or any other configurations suitable for holding the supporting member to the breast.

In some embodiments, an elastic membrane or pad 305 is fitted within the tissue-engaging surface of cup like supporting member. Optionally, membrane 305 is disposable, and can be replaced between patients. Optionally, membrane 305 is shaped and/or sized to cover at least a portion of the tissue engaging surface of the supporting member.

FIGS. 4A-B schematically illustrate shaping of the breast, according to some embodiments of the invention.

In some embodiments, shaping of the breast is performed before and/or during application of force to the tissue. In some embodiments, the breast 400 is shaped relative to the thoracic cage 408, for example substantially flattened against the thoracic cage 408 (see FIG. 4A) or instead compressed in a radially inwards direction of the breast to extend substantially perpendicularly to the thoracic cage (see FIG. 4B).

In some embodiments, shaping is performed before and/or during application of force to the tissue. Optionally, shaping is performed to move the tissue so as to allow access to tissue regions that are not or less accessible in a natural position of the breast, for screening those tissue regions.

In some embodiments, the screening device is configured for shaping the breast. Optionally, cup-like supporting member 402 comprises two or more base configurations (e.g. 2, 3, 4, 6, 8 or intermediate, larger or smaller number of base configurations), each configuration suitable to force the breast received within the cup into a predefined shape.

In some embodiments the supporting member comprises separately inflatable chambers that can be inflated to shape the breast. Optionally, these shaping chambers are configured radially outwardly relative to the force applying units of the member (which, in some embodiments, comprise of inflatable chambers as well).

In some embodiments, an inflatable chamber is configured to push the tissue when inflated, for example push the tissue against the thoracic cage. In an example, the inflatable chamber is configured to push the tissue at least 0.5 cm, at least 1 cm, at least 2 cm or intermediate, higher or lower distances relative to the initial tissue position.

In some embodiments, the device controller is configured to change between different configurations of the supporting member, for example by controlling inflation of the shaping chambers. Additionally or alternatively, shaping is performed manually, for example by shaping the breast before fitting the supporting member onto the tissue and/or by shaping the supporting member when the breast is already received within it.

In some embodiments, the force pattern applied by the device is selected in accordance with a current shape profile. Alternatively, the shape profile is selected in accordance with the force pattern to be applied. In the example shown herein in FIG. 4A, force 410 is applied along a transverse plane of the patient, compressing the breast 400 against the thoracic cage 408. In the example shown herein in FIG. 4B, force is applied from opposing sides of the breast in a radially inwards direction to compress the tissue in between.

In some embodiments, additionally or alternatively to shaping the breast, a position of the patient is changed, for example the patient lifts their arm or extends both arms backwards and/or inhales deeply, thereby stretching the breast tissue.

Optionally, the patient's position is changed to compress the breast tissue against the inner side of the supporting member. In some embodiments, the device is configured to automatically provide visual and/or oral instructions to the patient to change their position (e.g. lift arm, lie down, sit up, inhale, exhale and/or other positions or maneuvers). In some embodiments, changes in position and/or other maneuvers are performed simultaneously (e.g. arm lift is performed together with inhalation).

FIGS. 5A-E are exemplary spatial force patterns for applying onto breast tissue, according to some embodiments of the invention.

In some embodiments, the device is configured to apply force in one or more spatial patterns. The exemplary patterns shown in FIGS. 5A-D include applying force in a radially outward and/or radially inward directions (FIG. 5A); applying force in vertical strips (FIG. 5B); applying force in a spiral pattern, in an inward direction towards the nipple or in an outward direction towards the periphery (FIG. 5C); applying force in an arcuate pattern (FIG. 5D) and/or other force patterns or combinations thereof.

Figure 5A:
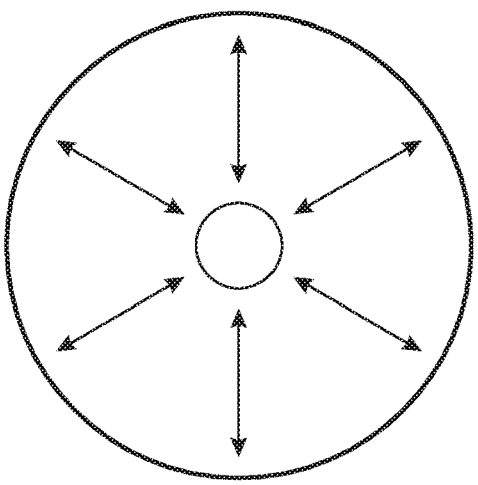
Figure 5B:
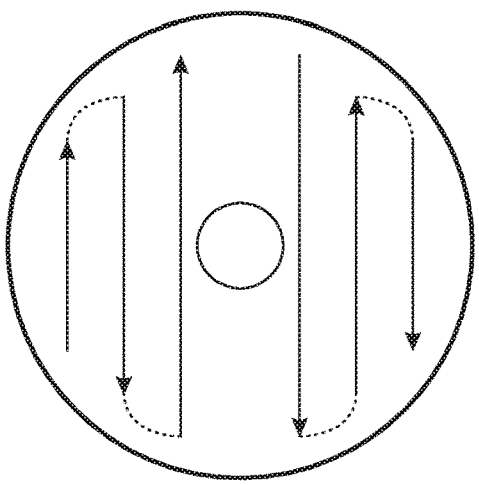
Figure 5C:
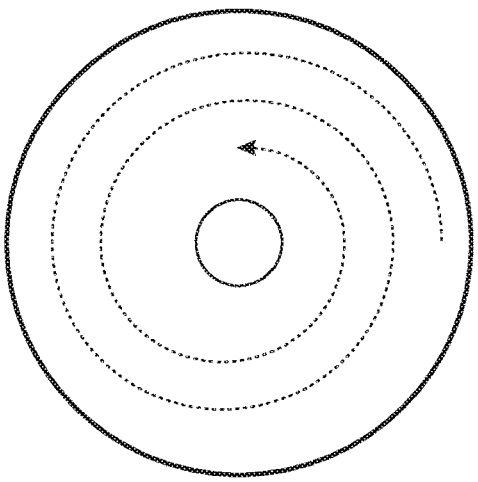
Figure 5D:
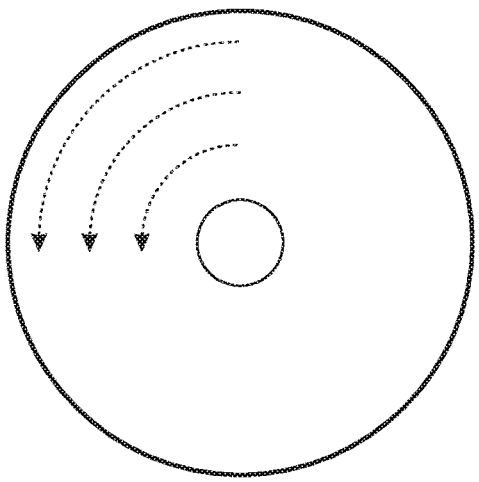
Figure 5E:
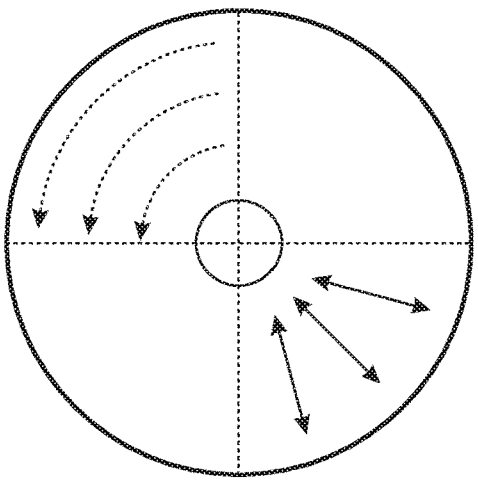

In some embodiments, for example as shown in FIG. 5E, the breast is divided into a plurality of regions, e.g. quadrants. Optionally, different force patterns are applied to different regions. Optionally, force patterns are applied to one or more regions and not applied to one or more other regions of the breast.

FIGS. 6A-D show various effects on the tissue in response to applying force at different directions and/or magnitudes, according to some embodiments of the invention.

FIGS. 6A-D schematically illustrate how force 600 (generally denoted by the black arrows) applied by one or more units of the array onto the breast tissue 602 moves, pushes, pinches, compresses, and/or otherwise deforms the tissue to detect a lump.

Figure 6A:
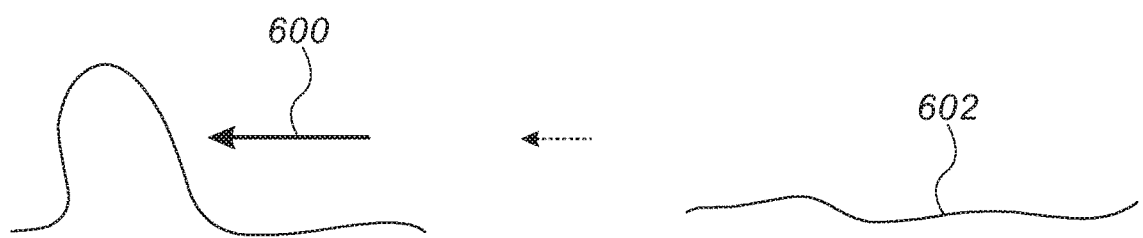
Figure 6B:
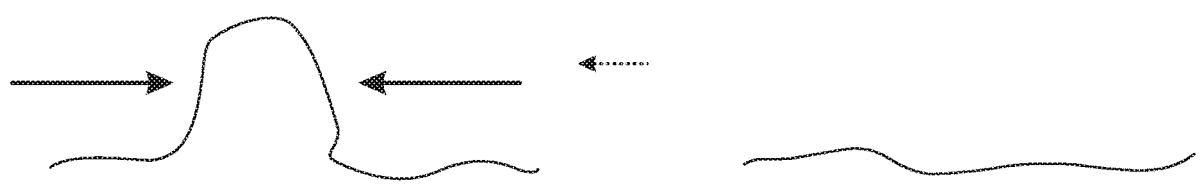
Figure 6C:
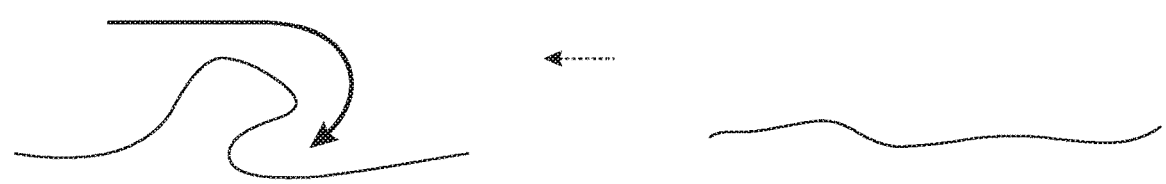
Figure 6D:

In the examples shown herein, FIG. 6A schematically illustrates pushing of the tissue laterally; FIG. 6B schematically illustrates forces applied from opposing directions to compress (pinch) the tissue in between (for example by actuating spaced apart force applying units); FIG. 6C schematically illustrates hooking of the tissue; and FIG. 6D schematically illustrates applying force substantially perpendicularly to the tissue surface, optionally compressing the tissue against the thoracic cage.

In some embodiments, the applied force moves the tissue in lateral, posterior, superior and/or inferior directions of the patient.

In some embodiments, force applied to the tissue acts to move the lump directly. Alternatively, force applied to the tissue acts to move normal tissue adjacent the lump, thereby moving the lump.

In some embodiments, a sudden giveaway of tissue in response to applying of force (optionally observed as a reduction in the pressure exerted by the tissue onto the sensing units) is indicative of a lump. In some embodiments, a high degree of tissue firmness (optionally observed as an expected resistance of the tissue to the applied force) is indicative of a lump. In some embodiments, a change in the tissue resistance to the applied force over time (optionally observed by comparing current screening results to previous screening results of the patient) is indicative of a lump.

FIG. 7 schematically illustrates a wearable screening device 700 comprising a plurality of inflatable chambers 702, according to some embodiments of the invention.

In some embodiments, cup-like supporting member 704 comprises or is formed of a plurality of inflatable chambers 702, functioning as the force applying and/or sensing units. In some embodiments, each of the chambers is independently inflatable and/or deflatable. In some embodiments, each chamber comprises an elastic tissue engaging face 706 configured to be in contact with a portion of the tissue surface and to apply known force to the tissue surface when inflated.

In some embodiments, an inflatable chamber 702 comprises one or more pressure sensors 708. In some embodiments, sensor 708 is mounted on tissue engaging face 706 of the chamber, so as to sense pressure exerted by the tissue onto the chamber. Additionally or alternatively, a change in inflation pressure of the chamber in response to pressure exerted onto the chamber (onto tissue engaging face 706) by the tissue is detected.

In some embodiments, device 700 is coupled to an inflation fluid source 710, comprising a gas (e.g. air), a mixture of gases, a liquid (e.g. water, oil) gel, and/or combinations thereof suitable for inflating the chambers. In some embodiments, fluid is introduced via tubing 712.

In some embodiments, control over the inflation level of the chambers is provided by controlling operation of a pump 714. Additionally or alternatively, control over the inflation level of the chamber is provided by moving one or more valves 716 to an open, close or partially-open position. Optionally, valve 716 is a bi-directional valve.

FIGS. 8A-B are a flowchart (8A) and a schematic illustration (8B) of exemplary activation of an array of force applying and/or sensing units, according to some embodiments of the invention.

In some embodiments, force applying and/or sensing units are arranged in an array 800 shaped and sized to fit the breast (e.g. a substantially circular cup like array).

In an exemplary activation pattern of the array, a unit (802, see FIG. 8B) is selected to apply force to the tissue (see step 801, FIG. 8A). In the example of a unit in the form of a rod, force may be applied by projecting the rod outwardly to compress the tissue. In the example of a unit in the form of an inflatable chamber, force may be applied by inflating the chamber to apply a known pressure onto the tissue.

In some embodiments, the tissue response to the applied force is sensed via one or more units adjacent the selected force applying unit (803, FIG. 8A), for example via a plurality of units 804 surrounding unit 802 (the sensing units 804 are marked by a dashed circle, FIG. 8B).

FIG. 9 shows a bra-shaped device 900 for screening breast tissue, according to some embodiments of the invention.

In some embodiments, device 900 comprises two cup-like supporting members 902, each contoured to fit one breast. In some embodiments, an array of force applying and/or sensing elements 904 is embedded within supporting member 902. Additionally or alternatively, array 904 is disposed on an inner lining of supporting member 902, facing the tissue.

In some embodiments, in which array 904 comprises inflatable chambers, the array is operably coupled to an inflation fluid source 906.

In some embodiments, device 900 is connected to a power source 908, for example a rechargeable battery.

In some embodiments, device 900 is in wired or wireless communication with a control module 912, configured to control application of force to the tissue and to process the sensed signals.

In some embodiments, device 900 is in wired or wireless communication with a user interface 910. In some embodiments, user interface 910 is configured to present the screening results to the patient and/or physician. In some embodiments, user interface 910 is configured to receive one or more patient-related input parameters from the patient and/or physician (such as age, weight, medical condition, breast size and/or other parameters). In some embodiments, user interface 910 is configured to receive results of previous examination. In some embodiments, user interface is configured to receive one or more operational parameters and to communicate these parameters to the control module 912, such as force applying protocols, screening duration, and/or other parameters.

In some embodiments, operation of the device is controlled by control module 912 in accordance with input parameter and/or protocols selected via user interface 910. Additionally or alternatively, control module 912 automatically selects operation protocols according to the inserted data.

In some embodiments, supporting member 902 is configured to sense a size and/or volume of the tissue received within it. Optionally, control module 912 automatically determines what force pattern(s) and/or intensities to apply according to the sensed tissue size and/or volume and/or type. Optionally, the extent of deformation of the tissue produced by applying force is selected in accordance with the tissue size and/or volume and/or type.

In some embodiments, supporting member 902 is adjusted to fit the breast, for example by tightening of straps. Optionally, once fit is obtained, a volume of the breast can be determined.

In some embodiments, device 900 is configured to screen both breasts simultaneously. Optionally, screening of one of the breasts or a certain region thereof is repeated automatically upon detecting a lump.

In some embodiments, bra-shaped device is designed to align the arrays with respect to the breasts and/or with respect to the body form, for example to center the array with respect to the nipple.

In some embodiments, the device is modular and comprises two supporting members that can be attached or separated from each other. Optionally, supporting members of various sizes are provided so that a suitable supporting member can be selected for fitting each of the breasts. This may be especially advantageous for patients having asymmetrical breasts. In some embodiments, bra shaped device 900 comprises one or more cameras 914 configured for obtaining an image of one or both breasts.

In some embodiments, cameras 914 are positioned at the tissue-facing side of the device. In some embodiments, cameras 914 are positioned such that they are located a distance away from the breast during wearing and/or taking off of the bra, so that an image can be taken before and/or following screening. Optionally, a patient (either sitting or standing up) stretches her arm forward to hold the device a certain distance away from her chest, for example such that cameras 914 are located at least 5 cm, at least 10 cm, at least 30 cm or intermediate, longer or shorter distances from the breast. In some embodiments, control module 912 operates one or more cameras 914 to produce one or more images of the breast.

In some embodiments, two or more images are acquired, each at a different patient position. For example, a first image is taken (optionally prior to screening) while the patient sits upright before and/or during wearing the device; and a second image is taken (optionally following screening) at a supine position. A potential advantage of acquiring images at different patient positions may include providing for visual inspection of tissue areas which may not be visible at one position, for example tissue areas behind the infra mammary fold and/or other tissue folds.

FIGS. 10A-C are graphical representations of tissue resistance sensed in the presence of a lump in the tissue, according to some embodiments. In the example shown herein, force applied to a tissue region in 3 different directions produces a tissue response that may be indicative of a lump. Optionally, the resistance of the tissue to the applied force is sensed by the device, for example by sensing pressure exerted by the tissue surface onto one more sensing units of the supporting member.

The profile described herein in FIGS. 10A-C may match a situation in which the lump exhibits a higher stiffness than the surrounding tissue. In FIG. 10A, lateral force applied from left to right (starting from left of the lump) results in a resistance profile that increases as the tissue adjacent the lump is pushed against the lump, climbing to a higher, optionally constant resistance when encountering the lump itself.

In FIG. 10B, transverse force is applied from the top of the lump (e.g. to compress the tissue against the thoracic cage), encountering high resistance caused by the stiff lump. In FIG. 10C, force is applied in a direction opposite to the force described in FIG. 10A (i.e. from right to left, starting from right of the lump), resulting in a substantially similar resistance profile.

FIGS. 11A-B are graphical representations of tissue resistance sensed in the presence of a lump in the tissue, according to some embodiments.

In FIG. 11A, different from the situation described in FIG. 10A, a sudden fall in tissue resistance in response to the applying of force may indicate the presence of a lump. Generally, in some embodiments, a sudden rise or sudden fall in tissue resistance (e.g. a sudden giveaway of the tissue) may indicate a border between tissues of different consistencies (e.g. a lump and normal tissue).

FIG. 11B shows an example in which pressure sensed in the presence of a lump (indicated by the dashed line) is substantially higher than pressure sensed in the same tissue when a lump is not present (indicated by the continuous line). Optionally, pressure sensed in the presence of a lump remains constant as long as force is applied.

FIG. 12 illustrates a supporting member comprising a plurality of inflatable chambers, according to some embodiments of the invention.

In some embodiments, supporting member 1200 comprises a plurality of inflatable chambers 1202. Optionally, each chamber is connected to a tube 1204 through which fluid is delivered to and/or from the chamber. In some embodiments, tube 1204 extends to a pumping unit 1206.

In some embodiments, a main conduit 1208 extends from the pumping unit and then splits into a plurality of narrower tubes, each delivering fluid to one or more chambers.

In some embodiments, inflation level is controlled with the aid of a valve 1208, optionally a bi-directional valve. In some embodiments, the device controller is configured to control opening, closing and/or partial opening of the valve to allow fluid in and/or out of the chamber. Optionally, valve 1208 is located at an opening of tube 1204 leading to chamber 1202.

In some embodiments, the chambers are inflated successively, for example in a time sequence that produces a spatial pressure wave for applying onto the tissue.

Additionally or alternatively, one or more chambers are inflated simultaneously.

In some embodiments, the supporting member further comprises a roller and/or ball suitable to roll across the inflatable chambers, for example across an outer surface of the chambers.

FIG. 13 is a schematic illustration of a device comprising an extension for screening the breast tail, according to some embodiments.

In some embodiments, the device comprises an extension 1300 shaped and/or sized for screening the breast tail. Optionally, extension 1300 forms an add-on that can be attached or removed from the supporting member 1302.

In some embodiments, extension 1300 is shaped to contact the breast tail, a tissue area between an upper quadrant of the breast and the ipsilateral axilla.

In some embodiments, extension 1300 is configured to apply force in one or more patterns, such as in a linear pattern 1304 in which force is applied, for example, against the pectoralis major muscle.

In some embodiments, the device comprises a second extension 1306, which is configured for screening the axilla, for example the area configured directly under the shoulder joint. In some embodiments, second extension 1306 is shaped to fit into the axilla. Optionally, second extension 1306 comprises an inflatable element that can be filled with fluid when positioned at the under arm location. In some embodiments, second extension 1306 is inflated until contact with the underarm tissue is achieved, to enable applying of force to that tissue region.

In some embodiments, the breast tail extension 1300 is configured to apply force against extension 1306 to compress the tissue in between.

FIGS. 14A-B are illustrations of bra shaped devices comprising breast tail and/or axillary extensions, according to some embodiments.

FIG. 14A shows a bra shaped device comprising a first extension 1400 configured for screening the breast tail, and a second extension 1402 configured for fitting inside the axilla.

In some embodiments, first extension 1400 is shaped and sized to fit the breast tail region, comprising an elongated profile. In some embodiments, second extension 1402 is shaped and sized to fit into the axilla, for example comprising a rounded egg-shaped profile. In some embodiments, second extension 1402 comprises an inflatable cushion, which can be inflated until obtaining fit with the axilla of the patient.

In some embodiments, the device comprises one or more adjustable straps 1408. Optionally, the straps can be pulled or released to ensure fit between the cup-like member and the breast and/or between the axillary extensions and the axilla region tissue.

FIG. 14B shows a bra shaped device including axillary extensions, in which the cup-like supporting members and/or the axillary extensions comprise inflatable chambers, according to some embodiments. In some embodiments, the chambers are connected to a fluid reservoir 1404, optionally including a pumping unit 1406 for directing fluid to and/or from chambers.

In some embodiments, control of operation is provided by control module 1410. Optionally, control module 1410 is connected to the device via one or more wires 1412. Additionally or alternatively, control module 1410 is connected to the wearable device via wireless connection. Optionally, activation signals and/or sensed signals (such as sensed pressure signals) are transferred via the connection.

In some embodiments, the device is connected to a power source 1414, such as a battery.

FIGS. 15A-B are examples of pressure distribution maps of a normal breast (15A) and a breast exhibiting a lump (15B), according to some embodiments.

In some embodiments, a pressure distribution map is produced based on the detected pressure signals. In some embodiments, a pressure distribution map of a screened breast is compared to a pressure distribution map of a healthy breast, for example compared to the second breast of the patient and/or to previous screening of the currently screened breast and/or to an expected pressure distribution calculated based on reference data (such as data obtained from a population).

In some embodiments, for example as shown in FIG. 15B, an irregular pattern of isobars 1500, such as isobars that are closely grouped to each other are indicative of a lump 1502 in the tissue.

It is noted that while some embodiments described herein discuss screening of breast tissue, methods and devices described herein may be used for screening of other tissue or organs. In such embodiments, the device may be contoured to fit the screened organ, for example having a tubular profile for receiving an organ within (e.g. a limb), a substantially flat profile for overlying a body surface, and/or other profiles suitable for applying force onto the tissue and sensing the tissue response.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A wearable device for breast screening, comprising:
at least one breast-contacting member shaped to contact a surface of a breast, the member comprising an array of force applying units and an array of sensors configured for sensing at least one parameter in response to force applied by the force applying units; the force applying units and the sensors disposed on or within the breast-contacting member and positionable to contact a surface of the breast, such that a plurality of force applying units of said array of force applying units are configured to contact the surface of a single breast;
a memory storing one or more patterns to be applied by the force applying units, the patterns suitable to detect a lump underlying the surface; wherein the pattern comprises a sequence of forces that vary spatially and/or vary in time;
a controller configured for reading data from the memory to automatically control application of force by at least some of the force applying units according to at least one of the patterns, the controller further configured for communicating with the array of sensors to receive signals associated with the at least one parameter sensed in response to the application of force, and to process the received signals to detect the lump.

2. The device according to claim 1, wherein the at least one parameter sensed by the sensors comprises pressure exerted by the breast onto the breast-contacting member in response to the applied force, and wherein at least some of the sensors comprise pressure sensors.

3. The device according to claim 1, wherein the controller is configured to process the received signals by comparing one or more received signals of a certain tissue region to one or more signals received from surrounding tissue to detect the lump.

4. The device according to claim 1, wherein the controller is configured to process the received signals by comparing one or more signals received from a certain tissue region to one or more signals received from the same tissue region when a different force pattern was applied.

5. The device according to claim 1, wherein the force applying units comprise a plurality of inflatable chambers, each chamber independently and controllably inflatable and deflatable, the inflatable chambers disposed within the member such that each chamber of the plurality of inflatable chambers has an elastic wall part configured to be in contact with a portion of the breast surface and to apply a known force to the portion of the breast surface when the chamber is inflated with an inflation fluid or air.

6. The device according to claim 1, wherein the force applying units comprises a moveable rod, a roller, or a bead.

7. The device according to claim 1, wherein the force applying units are configured to apply force along a transverse plane, a sagittal plane and/or a coronal plane of a patient screened using the device.

8. The device according to claim 1, wherein the controller is configured for processing the received signals to determine at least existence of the lump by comparing the signals to a reference table or to results of previous screenings of the patient.

9. The device according to claim 1, wherein the controller is configured for processing the received signals to determine borders of the lump.

10. The device according to claim 1, wherein the controller is configured for processing the received signals to determine a volume of the lump.

11. The device according to claim 1, wherein the controller is configured for processing the received signals to determine a stiffness of the lump.

12. The device according to claim 1, wherein the device further comprises a chemical sensor attached to the member such that the chemical sensor is in contact with a nipple of the breast for obtaining information about one or more chemical constituents of a secretion discharged from the nipple.

13. The device according to claim 1, wherein the device is configured to be self-operated by a patient using the device.

14. The device according to claim 1, wherein the breast-contacting member is configured for shaping the breast.

15. The device according to claim 14, wherein the controller is configured to select a screening protocol automatically according to a current shape of the breast.

16. The device according to claim 1, wherein the controller is configured to map the received signals.

17. The device according to claim 16, wherein the controller is configured to detect a location of the lump relative to the surface of the breast or relative to a thoracic cage adjacent the breast.

18. The device according to claim 1, wherein the device comprises one or more cameras configured for acquiring an image of the breast.

19. A method of screening breast tissue for early detection of cancer, comprising:
   providing a wearable device contoured to fit a shape of a breast;
   automatically applying force, by an array of force applying units, to the breast tissue using the device, the force applied in at least one pattern selected to detect a lump underlying a surface of the breast; the pattern comprising one or more forces that vary spatially and/or vary in time;
   automatically sensing, by an array of sensors, a tissue response of said breast tissue to the applying of force to thereby receive force-related signals; and
   analyzing the received force-related signals to identify the lump in the breast.

20. The method according to claim 19, further comprising producing a pressure distribution map of the received force-related signals.

* * * * *